(12) United States Patent
McKinnon et al.

(10) Patent No.: US 11,868,681 B2
(45) Date of Patent: Jan. 9, 2024

(54) SYSTEMS AND METHODS FOR OPTIMIZING FIT OF AN IMPLANT TO ANATOMY

(71) Applicant: Smith & Nephew, Inc., Memphis, TN (US)

(72) Inventors: Brian W. McKinnon, Arlington, TN (US); Ruxandra C. Marinescu Tanasoca, Memphis, TN (US); Randy C. Winebarger, Southaven, MS (US); William L. Bowers, Jr., Southaven, MS (US); James B. Wiebe, III, Coldwater, MS (US); Nathaniel M. Lenz, Germantown, TN (US); Zachary C. Wilkinson, Germantown, TN (US); Sean M. Haddock, Germantown, TN (US); Ryan L. Landon, Olive Branch, MS (US)

(73) Assignee: SMITH & NEPHEW, INC., Memphis, TN (US)

( * ) Notice: Subject to any disclaimer, the term of this patent is extended or adjusted under 35 U.S.C. 154(b) by 530 days.

(21) Appl. No.: 17/166,105

(22) Filed: Feb. 3, 2021

(65) Prior Publication Data
US 2021/0157957 A1    May 27, 2021

Related U.S. Application Data

(63) Continuation of application No. 16/105,682, filed on Aug. 20, 2018, now Pat. No. 10,922,448, which is a
(Continued)

(51) Int. Cl.
*A61B 34/10* (2016.01)
*A61F 2/02* (2006.01)
(Continued)

(52) U.S. Cl.
CPC .............. *G06F 30/00* (2020.01); *A61B 34/10* (2016.02); *A61F 2/02* (2013.01);
(Continued)

(58) Field of Classification Search
CPC ... G06F 30/00; A61B 34/10; A61B 2034/104; A61B 2034/105; A61B 2034/108; A61B 2017/568; A61F 2/02
(Continued)

(56) References Cited

U.S. PATENT DOCUMENTS 5,280,792 A    1/1994   Leong et al.
2003/0216669 A1   11/2003   Lang et al.
(Continued)

FOREIGN PATENT DOCUMENTS

EP    0611160 A2    8/1994
EP    1413264 A2    4/2004
(Continued)

OTHER PUBLICATIONS

Australian Patent Examination Report No. 1 for AU2012283835 dated Apr. 20, 2016.
(Continued)

*Primary Examiner* — John E Johansen
(74) *Attorney, Agent, or Firm* — KDW Firm PLLC

(57) ABSTRACT

A system and method for pre-operatively optimizing a fit of an orthopaedic implant relative to a particular individuals anatomy is provided. The method includes: receiving information including a three-dimensional anatomic model of the individuals anatomy; computing a periphery of a simulated resection portion of the anatomic model without reference to any abnormal morphology; identifying a preliminary size for an orthopaedic implant component for use on the simulated resection surface; initially positioning the orthopaedic implant model relative to the simulated resection portion;
(Continued)

generating random point sets around the peripheries of the simulated resection portion and the orthopaedic implant model; utilizing a position optimizer to determine whether the position of the orthopaedic implant periphery relative to the simulated resection portion periphery is optimal; determining whether the selected orthopaedic implant model results in overhang; and verifying the position of the orthopaedic implant and/or the size of the orthopaedic implant.

22 Claims, 21 Drawing Sheets

Related U.S. Application Data continuation of application No. 14/232,958, filed as application No. PCT/US2012/047647 on Jul. 20, 2012, now Pat. No. 10,102,309.

(60) Provisional application No. 61/511,713, filed on Jul. 26, 2011, provisional application No. 61/509,928, filed on Jul. 20, 2011.

(51) Int. Cl.
*A61B 17/56* (2006.01)
*G06F 30/00* (2020.01)

(52) U.S. Cl.
CPC ... *A61B 2017/568* (2013.01); *A61B 2034/104* (2016.02); *A61B 2034/105* (2016.02); *A61B 2034/108* (2016.02)

(58) Field of Classification Search
USPC .............................................................. 703/1
See application file for complete search history.

(56) References Cited

U.S. PATENT DOCUMENTS

| | | | |
|---|---|---|---|
| 2007/0233267 A1 | 10/2007 | Amirouche et al. | |
| 2007/0255288 A1* | 11/2007 | Mahfouz ............. | A61B 5/1075 606/102 |
| 2008/0154127 A1 | 6/2008 | DiSilvestro et al. | |
| 2008/0319448 A1* | 12/2008 | Lavallee ................ | G06F 30/00 703/11 |
| 2009/0043556 A1* | 2/2009 | Axelson ................ | G06F 30/00 600/416 |
| 2009/0204222 A1 | 8/2009 | Burstein et al. | |
| 2009/0228113 A1 | 9/2009 | Lang et al. | |
| 2009/0264894 A1* | 10/2009 | Wasielewski ........... | A61F 2/389 703/1 |
| 2009/0274350 A1 | 11/2009 | Pavlovskaia et al. | |
| 2010/0049195 A1 | 2/2010 | Park et al. | |
| 2010/0076563 A1* | 3/2010 | Otto ....................... | G16H 20/30 623/20.14 |
| 2010/0153081 A1 | 6/2010 | Bellettre et al. | |
| 2011/0029093 A1* | 2/2011 | Bojarski .............. | A61F 2/30942 623/20.14 |
| 2011/0092804 A1 | 4/2011 | Schoenefeld et al. | |
| 2012/0143090 A1 | 6/2012 | Hay et al. | |
| 2014/0244220 A1 | 8/2014 | McKinnon et al. | |
| 2016/0217268 A1 | 7/2016 | Otto et al. | |

FOREIGN PATENT DOCUMENTS

| | | |
|---|---|---|
| EP | 2734140 A1 | 5/2014 |
| JP | 1074934 A | 1/1995 |
| JP | 2008264947 A | 11/2008 |
| JP | 2009056299 A | 3/2009 |
| JP | 2014521835 A | 8/2014 |
| WO | 2011007806 A1 | 1/2011 |
| WO | 2013013170 A1 | 1/2013 |

OTHER PUBLICATIONS

Chinese Decision of Rejection dated Dec. 16, 2016.
Chinese First Office Action for 20128045854 dated Sep. 14, 2015.
Chinese Second Office Action for 20128045854 dated Jun. 14, 2016.
European Office Action for 128155669.4 dated Mar. 13, 2017.
European Office Action for 13763527.2 dated Sep. 13, 2016.
European Search Report and Written Opinion for 12815569.4 dated Mar. 6, 2015.
India Office Action for 1344/DELNP/2013 dated Dec. 9, 2019.
International Search Report and Written Opinion for PCT/US2012/047647 dated Oct. 12, 2012.
Japan Decision of Rejection for 2014521835 dated Apr. 3, 2017.
Japanese Office Action for 2014521835 dated Jun. 27, 2016.
Mexican Office Action for MX/a/2014/000752 dated Feb. 1, 2018.
Russian First Office Action for 2014101264 dated May 13, 2016.
Russian Second Office Action for 2014101264 dated Jul. 20, 2017.
Chinese Third Office Action, Chinese Patent Office, Chinese Patent Application No. 201710969849.3, dated Jan. 20, 2020, 9 pages.

* cited by examiner

SYSTEMS AND METHODS FOR OPTIMIZING FIT OF AN IMPLANT TO ANATOMY

CROSS-REFERENCE TO RELATED APPLICATIONS

This application is a continuation application of U.S. patent application Ser. No. 16/105,682, filed on Aug. 20, 2018, and titled "Systems and Methods for Optimizing Fit of an Implant to Anatomy," which is a continuation application of U.S. patent application Ser. No. 14/232,958, filed on Mar. 21, 2014, and titled "Systems and Methods for Optimizing Fit of an Implant to Anatomy," which claims the benefit of PCT International Application No. PCT/US2012/047647, filed on Jul. 20, 2012, which claims the benefit of U.S. Provisional Application No. 61/509,928 filed on Jul. 20, 2011 and U.S. Provisional Application No. 61/511,713 filed on Jul. 26, 2011. The disclosure of each application is incorporated by reference in its entirety.

STATEMENT REGARDING FEDERALLY SPONSORED RESEARCH OR DEVELOPMENT

Not Applicable.

APPENDIX

Not Applicable.

BACKGROUND OF THE INVENTION

A common problem with joint arthroplasty procedures, such as knee arthroplasty in which the articulating surfaces of the knee joint are resected and replaced with implants, is that the implants often do not optimally cover the resected surfaces of the patient's anatomy. Typical implant sets only provide a few size options, and, given the variability of bone and other anatomy morphology from individual to individual, the closest size for the particular patient will often result in the outer periphery of the implant either overhanging the resected surfaces, and/or not entirely covering portions of the resected surfaces. Either situation is undesirable and sometimes can lead to problems, such as soft tissue irritation or functional compromise.

Many times in total knee arthroplasty (TKA), poor post-operative patient outcomes are not caused from a poorly-designed prosthesis. Instead, the problem may often stem from a well-designed prosthesis being installed in a less-than-optimal biomechanic position relative to the natural anatomy of the patient in an attempt to get the best anatomic fit. In other words, the probability of revision knee surgery due to pain or abnormal wear may be high even with a well-designed knee-prosthesis if said prosthesis is misaligned or if the prosthesis is installed without considering the biomechanic effects of prosthetic orientation.

In total knee arthroplasty (TKA), a surgeon may determine the size of a femoral knee implant component by measuring the A-P width of the distal femur from an anterior coronal plane to a posterior coronal plane. Bone sizing is done to determine the closest size femoral component without notching the anterior femoral cortex. Due to noticeable gaps in A-P width between sizes of femoral components within a particular orthopedic product portfolio, the biomechanic fit, feel, and function of the implant is compromised in three different ways for three different techniques, respectively.

First, if a surgeon decides to use a posterior referencing technique, the anterior flange of the femoral component implant will fall where it may depending on the anterior-posterior size of the implant. In many cases, a patient's bone size falls between the sizes dictated by an orthopaedic product offering. While providing better bone coverage, using a larger sized implant with a posterior referencing technique can lead to patella stuffing, retinacular stretch, patello-femoral ligament stretch, quadriceps and patellar tendon over-stretching, quad inefficiency, and anterior knee pain due to increased forces on the patella. Conversely, using a smaller sized implant with a posterior referencing technique might cause loose quadriceps and patellar tendons, patellar subluxation, poor patellar tracking, and knee joint instability/laxity.

Second, if a surgeon decides to use an anterior referencing technique, one or more posterior condyles of the femoral component(s) will fall where they may depending on their sizes and geometries. In many cases, a patient's bone size falls between the sizes dictated by an orthopaedic product offering. While providing better bone coverage, using a larger sized implant with an anterior referencing technique can lead to increased collateral ligament tension, a tight-joint in flexion, decreased range of motion, and increased risk of injury to soft tissues such as the ACL and PCL. Conversely, using a smaller sized implant with an anterior referencing technique might cause joint laxity in deep flexion, loose collateral ligaments, and pseudo-patellar baja if a thicker tibial insert is used to compensate for the laxity in flexion.

Third, while it is uncommon to do so, if a surgeon decides to take a middle-of-the-road technique (i.e., arbitrarily referencing somewhere between anterior referencing and posterior referencing), there may be a combination of the aforementioned disadvantages, or there may be a more ideal implant position than what is chosen based purely upon anatomic fit and non-kinetic intra-operative ligament balance.

Software programs that simulate in-vivo functional activities (e.g., LifeMOD/KneeSIM, a product of LifeModeler, Inc. of San Clemente, Calif.), have been used for the purpose of evaluating the performance of implant designs. Such programs use a three-dimensional, dynamics-oriented, physics-based modeling methodology. While these programs have been used to design implant geometries in the past, the prior art has not utilized such software to fine-tune the anatomical placement or sizing of implants (i.e., standard and custom) so that they meet and exceed an individual patient's needs. U.S. Pat. No. 8,078,440 issued to Otto et al. on Dec. 13, 2011 discloses a system and method that uses such software programs for preoperatively characterizing an individual's biomechanic function in preparation of implanting a prosthesis. U.S. Pat. No. 8,078,440 is herein incorporated by reference in its entirety.

SUMMARY OF THE INVENTION

It is in view of the above problems that the present invention was developed. The invention is a system and method for addressing these issues that utilize a large family of implant sizes featuring a variety of outer periphery shapes. The best fitting implant may be identified from this family by simulating planned resections on a three-dimensional model of the patient's anatomy. Once the planned resection or resections are simulated, the perimeter of those resection(s) can be compared to the various implant sizes or size groups and possible positions of those implants to identify the best fitting implant or implants. If several implants are identified as "best fitting," other criteria/dimensions could be considered to narrow the possible implants to a single or smaller group.

In one aspect of the invention, the three-dimensional model of the patient's anatomy may be created from pre-surgically acquired imaging data, such as MRI, CT or other imaging data and modified to reflect planned resections to the anatomy. Three-dimensional CAD or other models of the implants can be overlaid over the modified three-dimensional model of the patient's anatomy. Manual or automated computer programs may be used to compare outer peripheries of the implant models to the modified anatomic model. The computer programs may utilize decision rules to identify the optimal implant models.

In order to improve biomechanic performance, there is provided a system and method for determining the best biomechanic sizing of components for a given prosthesis and patient. Biomechanic sizing (e.g., kinetic sizing) may be defined as a step of determining an optimum implant component size, such that when said implant component is installed in an optimum orientation and configuration suggested by simulation model results, it will provide the most natural and optimum force environments, range of motion, feeling, and biomechanic patterns for a particular patient. In general, sizing implies different dimensions of size and not necessarily options of geometry, such as articular geometry, although changes of geometry may be included in some embodiments. Good biomechanic sizing may require slight overhang of an implant or slightly less bony coverage than would typically be desirable according to conventional methods but will potentially increase the probability of patient satisfaction during post-operative activities. For example, a small tri-compartmental femoral component positioned in a first orientation on an individual patient that results in less bone coverage may provide higher functional biomechanic performance values than a larger tri-compartmental femoral component positioned in a second orientation that provides better bone coverage. In this instance, the small tri-compartmental femoral component is considered to be better biomechanically-sized than the larger tri-compartmental femoral component.

Sizing through biomechanics allows for identification of whether the current implant "mismatches" biomechanically and prompts a change in shape of the implant to reduce unwanted stresses and/or kinematics. Further, a range of constraint may be desirable for a particular patient. For example, older patients have poor proprioception, so the performance envelope shrinks to provide them a sense of greater stability, whereas a younger patient has good balance and wants greater range of motion, so the performance envelope is enlarged accordingly. This is somewhat similar to the intraoperative decisions of a surgeon, but the computer provides a more comprehensive analysis of the kinetic trade-offs and proper implant selection.

In all instances, a surgeon has the opportunity to make compromises as he or she sees fit, through the use of modular implants or a larger implant selection. A surgeon may, at any time, abandon the recommendations generated from the computer simulations of the invention. The invention primarily serves to give a surgeon more options to consider both before and during surgery. The invention does not reduce the number of options permitted.

According to some embodiments, there is provided a method of tuning the orientation of one or more prostheses prior to implantation to give the best biomechanic performance, somewhat regardless of bone fit as conventionally done. First, a forward dynamic computer model of virtual patient is created. Such model may be created with BodySIM software by LifeMOD. The model is then used to "virtually" implant one or more prostheses (e.g., TKA component, uni-compartmental component, bi-compartmental component) into the patient and determine which configuration(s) and orientation(s) of said one or more prostheses yields the best biomechanic performance, range of motion, and soft-tissue force environment throughout designated activities. Depending on a patient's lifestyle demands, an ideal implant size, type, brand, and spatial orientation(s) for each component of a prosthesis is chosen based on iterative modeling and simulating. The prosthesis components are then implanted accordingly.

There is provided a method for pre-operatively optimizing a fit of an orthopaedic implant relative to a particular individual's anatomy. The method includes: receiving information including a three-dimensional anatomic model of the individual's anatomy; computing a periphery of a simulated resection portion of the three dimensional anatomic model without reference to any abnormal morphology using a processor; identifying a preliminary size for an orthopaedic implant component for use on the simulated resection surface; initially positioning the identified preliminarily orthopaedic implant model relative to the simulated resection portion of three-dimensional bone model; generating random point sets around the peripheries of the simulated resection portion and the orthopaedic implant model; utilizing a position optimizer to determine whether the position of the orthopaedic implant periphery relative to the simulated resection portion periphery is optimal; determining whether the selected orthopaedic implant model results in overhang relative to the three dimensional anatomic model; and verifying the position of the orthopaedic implant and/or the size of the orthopaedic implant.

In some embodiments, the method further comprises the step of creating a plurality of resection planes of the three-dimensional anatomic model.

In some embodiments, the method further comprises the step of generating a resection safe zone.

In some embodiments, the method further comprises the step of detecting abnormal morphology of the three dimensional anatomic model.

In some embodiments, the method further comprises the step of recording the preliminary size for the orthopaedic implant.

In some embodiments, the method further comprises the step of calculating minimum distances between point sets.

In some embodiments, the method further comprises the step of outputting information to a user sufficient to verify that the optimal implant size and position identified appears to be correct and that such identified implant size is appropriate for other components used for the surgical procedure.

In some embodiments, the method further comprises the step of repeating the steps of initially positioning the identified preliminarily orthopaedic implant model relative to the simulated resection portion of three-dimensional bone model and generating random point sets around the peripheries of the simulated resection portion and the orthopaedic implant model.

In some embodiments, the method further comprises the step of selecting a different size orthopaedic implant.

In some embodiments, the method further comprises the step of determining whether the previous iteration through the size optimization steps identified overhang for that implant model.

In some embodiments, the verification step is a semi or fully automated verification procedure.

BRIEF DESCRIPTION OF THE DRAWINGS

The accompanying drawings, which are incorporated in and form a part of the specification, illustrate embodiments of the present invention and together with the description, serve to explain the principles of the invention. In the drawings.

DETAILED DESCRIPTION OF THE DRAWINGS

Figure 1:
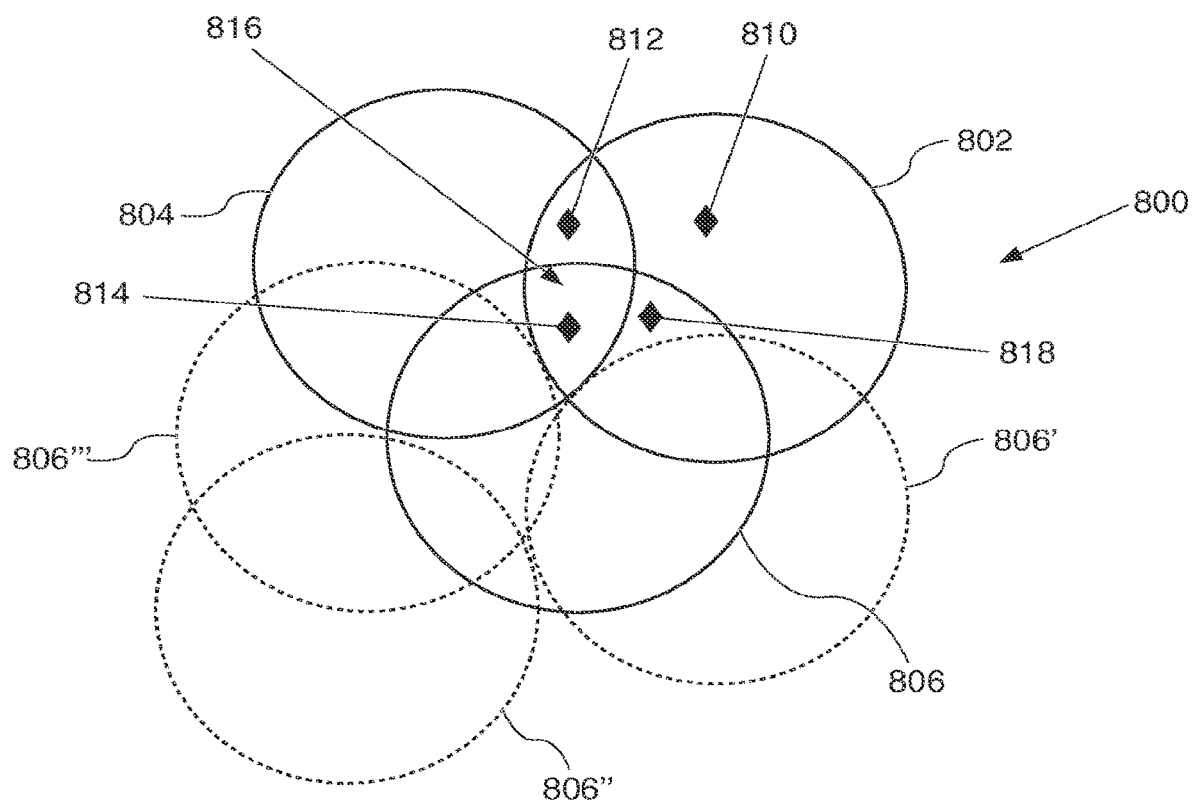
FIG. 1 is a schematic Venn diagram illustrating problems that currently exist in the prior art.

Referring to the accompanying drawings in which like reference numbers indicate like elements, FIG. 1 is a Venn diagram (800) illustrating problems encountered by prior art surgical methods. The diagram (800) comprises at least three prosthetic performance circles (802, 804, and 806). Performance circle (802) is representative of best anatomic fit for a given prosthesis. Ligament balance performance circle (804) is representative of best intra-operative ligament balancing that can be achieved without patient muscle input and other dynamic input. For instance, a good flexion/extension gap and good stability during trial reduction in TKA might place an overall prosthesis performance value (812) within the ligament balance performance circle (804).

Performance circles (806, 806', 806", 806''') are representative of the best expected biomechanic performance during various postoperative activities. Biomechanic performance circles (806, 806', 806", 806''') may move relative to the other performance circles (802, 804) or may become larger or smaller depending on: 1) how robust the prosthesis is to mis-implantaion, 2) how well the prosthesis geometries address all patients (including outliers) within a patient population, and 3) the activity from which performance is measured and based.

Conventionally, a surgeon selects a prosthetic component type and size that anatomically fits a patient the best, and then implants the prosthetic component in an orientation for best bony coverage and anatomic fit (e.g., in good mechanical axis alignment). The overall performance achieved from a prosthesis installed in such a way may be characterized as having a marginal or good overall prosthesis performance value (810). Overall prosthesis performance values (810) achieved purely based on good anatomical fit (802) are limited because: 1) flexion/extension gaps may not be optimized and may lead to unwanted laxity or stiffness throughout portions of a range of motion, 2) ligaments may not be balanced which may lead to pain or compensations during movement, and 3) prosthesis surface geometries are inherently compromised because they are designed to suit a large patient population and may insufficiently address the needs of every patient (e.g., "outliers").

In some embodiments, there is provided a method comprising the step of inputting a desired knee prosthesis product make and model number into a computer simulation model, the model simulating the individual patient's functional patterns or patterns very similar to those of the patient. The desired knee prosthesis may include without limitation, any one or more of a unicondylar femoral component, a patello-femoral component, a bi-compartmental femoral component, multiple unicondylar femoral components, a bi-compartmental femoral component in combination with a unicondylar femoral component, two unicondylar femoral components in combination with a patello-femoral component, a unicondylar tibial insert, a unicondylar tibial tray, a total bi-condylar cruciate-sparing tibial insert, a hi-condylar cruciate-sparing tibial tray, a bi-condylar cruciate-sacrificing tibial insert, a bi-condylar cruciate-sacrificing tibial tray, a patellar button, a patellar tray, fixed-bearing devices, mobile-bearing devices, total arthroplasty devices, hemi-arthroplasty devices, focal defect repairs, and combinations thereof. The step of inputting the desired knee prosthesis make and model number can be facilitated by a database of CAD files obtained from one or more orthopaedic manufacturers or third parties and stored on a server drive or the like. If custom prostheses are used, entire CAD files of the custom knee prosthesis to be implanted may be uploaded into the computer simulation model. The knee prosthesis CAD models imported into the computer simulation model may be two-dimensional (2D) models or three-dimensional (3D) models. The knee prosthesis models may be imported into a computer simulation model without specifying prosthetic component sizes, so that the computer simulation model can suggest an optimum size for each prosthetic component in addition to one or more optimum orientations corresponding to said optimum size.

For instance, a smaller-sized prosthetic component positioned in a first optimal orientation may yield better biomechanic performance (806) as compared with a larger-sized prosthetic component in a second optimal orientation. In other instances, for example, computer simulation modeling according the present invention may indicate that a size large patello-femoral component implanted in a first configuration with respect to a size small medial unicondylar femoral component yields the same or better performance characteristics for a given activity than a size small patello-femoral component implanted in a second configuration with respect to a size small unicondylar femoral component. Performance differences may be attributed to the tangency and transition between the patello-femoral component and the unicondylar femoral component. This information can be relayed to the surgeon before or during surgery. Using anatomic landmarks and measurement data gathered during patient characterization, either a computer simulation model or a CAS system can help the surgeon determine which relationships yield the best anatomic fit with no substantial decrease in biomechanic performance.

The computer simulation models generally simulate patient-specific biomechanic patterns for one or more various activities and may be iteratively run for a finite number of modeling iterations. During each modeling iteration, one or more input variables are incrementally changed or added according to the patient's functional characterization and functional envelope. Certain input variables may be given more weight and importance depending on the individual patient's needs and expectations. Input variables that are changed or added within the computer simulation models during each modeling iteration may include, for instance, the make and model of the desired implant, the size of each component of the desired implant, the anterior-posterior (A-P) positioning of each component of the desired implant, the medial-lateral (M-L) positioning of each component of the desired implant, the superior-inferior (S-I) positioning of each component of the desired implant, the internal-external rotation positioning of each component of the desired implant, the varus-valgus (i.e., abduction-adduction) positioning of each component of the desired implant, and the flexion-extension positioning of each component of the desired implant. It is to be understood that one of ordinary skill in the art would appreciate that many other input variables could be added or changed in the computer simulation models.

After the computer model simulations are completed, the software program, or a program separate from the software program compiles the expected biomechanic results for different implant configurations. Results may come in the form of tables of raw data corresponding to magnitudes and directions of force vectors, loads, shear stresses, and moments experienced by one or more of the implant components during each simulation iteration. Raw data may be stored in a database for subsequent implant design studies or to help create the characterization chart or lookup table mentioned later in this disclosure. Alternatively, raw data may be processed for clearer user analysis and interpretation by the surgeon. The data may even be distributed to the patient as a way of documenting and communicating the expected overall prosthesis performance of their artificial knee after it is implanted in them. The results are compiled and processed in order to determine the optimum positioning and sizing information for each knee prosthesis component, relative to the patient's anatomy. For instance, the computer simulation models described may export the raw data from iterative computer simulations into a data program preferably configured for statistical analysis (e.g., spreadsheet software or MATLAB by The MathWorks, Inc.). Then, the data program itself or another program linked thereto compiles the raw data and determines one or more optimal values for each input variable used in the iterative computer simulations. Knowing the optimal values for each input variable of the simulations helps a surgeon formulate a surgical plan specific to the measured patient. The surgical plan might include suggestions for strategically orientating bony cuts, holes, and ligamentous releases so as to provide optimum stresses and forces on the implant and surrounding soft tissues. Surgical recommendations and/or the expected biomechanic results may be presented to a surgeon or engineer through the use of charts, graphs, spreadsheets, or tables. The presented materials may be generated by the data program or the simulation software itself. For instance, after iterative modeling, computer simulation software may indicate: (1) the best prosthesis component sizes to use; (2) the best anterior-posterior (A-P) slope angles to use for each prosthesis component; (3) the best medial-lateral (M-L) orientations for each prosthesis component relative to bony anatomy; (4) the best superior-inferior (S-I) position for each prosthesis component (i.e., depth of proximal or distal bone cuts); (5) the best internal-external rotation position for each component of the prosthesis; (6) the best varus-valgus (i.e., abduction-adduction) angles to use for each prosthesis component; and (7) the best flexion-extension angles for each component of the prosthesis. In some embodiments, the computer simulation software may indicate a recommended surgical approach (such as anterior or posterior referencing), direction of saw-cut, or ligamentous release (such as the algorithm Whiteside uses). In some embodiments, the computer simulation software may indicate a recommended course of action based upon one or more chosen options. Such recommendations may be branched and hierarchical depending upon options chosen, like a choose your own adventure children's hook.

The computer simulation models may take into consideration stresses in the medial and lateral collateral ligaments (MCL, PCL), anterior cruciate ligament (ACL), posterior cruciate ligament (PCL), quadriceps muscle, patellar tendon, medial and lateral retinaculae, and other soft tissues during iterative simulation, and may, without limitation, suggest any one or more of: ligament release locations and amounts (e.g., depth of incision), prosthetic component orientations, and bone cut configurations that provide the most stability and lowest forces at the implant-hone interfaces.

Each database described herein may include any one or more of an image dataset, an imageless dataset, an equation, a tolerance, a geometric model, patient anatomical data, or a parameter relative to the anatomy. Databases may further comprise biomechanic function characterization data, anatomical landmark data (e.g., soft tissue attachment points), and data relating to various relative dimensions between anatomical landmarks. The databases may be used to develop one or more patient characterization charts or lookup tables by running hundreds of implant simulations to see which implant configurations provide the best results and most acceptable implant and soft tissue stresses for different generalized patient groups. Computer modeling software may reference the characterization charts, lookup tables, or databases in order to quickly determine which implant configurations to start with for a particular patient. For example, a patient is first assessed and characterized, and is then compared to a characterization chart compiled from data acquired by many cases. The characterization chart indicates which implant type(s), size(s), and relative spatial orientation configuration(s) are believed or statistically proven to work best for the characterization belonging to the particular patient. The implant may be installed based solely on the characterization chart, or the characterization chart may serve as a starting point for further computer simulations of the patient to fine-tune the size(s) and position(s) of one or more implant components.

Computer simulations of the patient may comprise body or knee simulations during one or more activities. Simulations may be facilitated by software such as LifeMOD./KneeSIM and BodySIM from LifeModeler, Inc. San Clemente, Calif. Implant sizes, geometries, and configurations are iteratively changed between simulations to obtain the best biomechanic performance (806) from a given prosthesis design. Prosthesis designs may also be iteratively changed between simulations if a surgeon does not have a preferred brand, or if biomechanic performance circles (806, 806', 806", 806''') for a given prosthesis and patient combination are too small or mutually exclusive to provide good anatomic fit. Good biomechanic fit helps lead to a more natural feeling to the patient and may help minimize shear forces at implant-bone interfaces.

Patient characterization and computer simulation may use anatomical landmarks of a patient alone or in combination with the aforementioned biomechanic function measurements. If both anatomic measurements (i.e., taken from bone models) and biomechanic measurements (e.g., taken from gait lab) are made, then both postoperative kinematic function (806) and bone fit performance (802) for a given prosthesis can be optimized to provide an increased overall performance value (818) to the patient.

The computer simulations described throughout this disclosure may comprise virtual patient computer models built from anthropometrics of the patient prior to surgery using any one or more of motion capture, force plate data, stair climb data, stair descend data, chair rise data, etc. The virtual patient computer model may also be built by CT or MR data of hones to allow anatomic fit (802), and biomechanic performance (806), and ligament balance (804) optimization. Once the virtual patient computer model is built, a surgeon or engineer can perform iterative virtual surgeries on the virtual patient to determine the best implant configurations for the patient's functional envelope. Iterations may be done manually or automatically through computer automation. Parameters such as femoral component size, type, brand, and spatial orientation are changed within the virtual patient model either manually or automatically for each iteration. For example, femoral joint line orientation, femoral varus/valgus orientation, femoral internal and external rotation orientation, femoral flexion/extension orientation, and other femoral spatial orientations may be iteratively changed within the model to "tune" a femoral component position for optimum results. Additionally, several parameters, such as tibial component size, type, brand, and spatial orientation, can be changed within the virtual patient model. For example, tibial internal and external rotation, tibial posterior slope, tibial A-P positioning, tibial varus/valgus orientation, as well as other tibial spatial orientations may be altered to "tune" a tibial component implant either alone or in combination with the abovementioned femoral component. Moreover, several parameters, such as patellar component size, type, brand, and spatial orientation relative to the femoral component and/or tibial component, can be changed within the virtual model to obtain a total configuration that yields the best implant performance characteristics for the particular patient's anatomy, biomechanic function, and lifestyle.

According to some embodiments, a surgeon may set up iterative virtual surgeries. After characterizing a patient's biomechanic function and/or anatomy using the methods described herein, the surgeon may virtually place one or more virtual implants on an individual patient's hone model for best bony coverage and mechanical alignment as he or she would conventionally do, only using simulation software. Then, the surgeon may define one or more ranges, thresholds, variables, limits, or parameters to set a size and spatial orientation envelope for the one or more virtual implants that represent the one or more implants to be implanted into the patient. For instance, an envelope for the one or more virtual implants may be defined by input received from surgeon or engineer prompts. Prompts may include, for example, maximum or minimum limits for implant size, changes in position (mm) in a medial-lateral direction, changes in position (mm) in an inferior-superior direction, changes in angular position (degrees) of internal/external rotation, changes in angular position (degrees) of varus/valgus, changes in angular position (degrees) of flexion/extension, and changes in position (mm) in an anterior-posterior direction. Computer simulations may then be run, with each iteration slightly modifying the position of the one or more implants within the defined envelope.

For example, a surgeon or engineer may first virtually size and virtually implant a virtual femoral component and a virtual tibial component into a virtual patient model for best bone fit and mechanical axis alignment as would conventionally be done; however, using software instead of an actual trial reduction step during surgery. This initial virtual sizing and virtual placement may be based on common techniques, such as using epicondylar axis and Whiteside's line to determine internal and external rotation or, in the case of a tibia, Akagi's line or the line from the extreme medial-lateral positions, and may be considered a crude start for optimizing biomechanic performance (806). The surgeon then requires that a maximum and/or minimum of N computer modeling simulation iterations (wherein, N is a specified number of iterative virtual surgeries) are used to virtually position the virtual femoral component differently within a spatial orientation envelope of +/−0.1 mm in a medial-lateral direction, +/−0.1 degrees of internal/external rotation, +/−0.1 degrees of varus/valgus, and +/−0.1 mm in an anterior-posterior direction, and a predetermined spatial orientation resolution of 0.1 mm and 0.1 degrees (i.e., the amount to change each input variable between simulation iterations).

After the virtual surgery simulations are finished and the data is compiled, one or more suggested sizes and/or relative spatial orientations of the virtual femoral component and virtual tibial component are displayed, along with one or more expected performance characteristics [e.g., expected metallic or polymeric volumetric wear rate, ligament tension (e.g., MCL, LCL, ACL if applicable, and PCL if applicable), range of motion, efficiency, stress environment(s), biomechanic environment(s), fixation strength, ligament balance, anatomic fit (e.g., bone fit), fixation force(s), implant longevity, tibiofemoral and patellofemoral kinematics throughout a range of motion (e.g., maximum flexion, maximum internal/external rotation, maximum patella flexion and tilt, maximum femoral rollback), quadriceps force] associated with said suggested sizes and relative spatial orientations. The surgeon may then decide to re-orient the components of the prosthesis based on expected performance characteristics calculated by the software in order to optimize anatomic fit and biomechanic performance.

Natural feeling (e.g., proprioception) and biomechanic performance of an implant can be better established if the implant is custom-designed or otherwise an implant specifically designed for use within a niche characterized patient population to which the patient belongs. For instance, an implant brand or type that is designed specifically for any one or more of the patient's race, build, religion (e.g., frequently used prayer stances), hobby (e.g., golf, biking, hiking), gender, activity level (high vs. low), and lifestyle may improve biomechanic performance when the novel installation tuning methods of the present invention are used.

The benefit of the present invention is that a surgeon can perform hundreds of virtual surgeries through the use of iterative analysis, in order to determine the optimal size, optimal placement, optimal spatial orientation, optimal alignment, and/or the best performance compromise between anatomic fit (802) and biomechanic function (806), all while taking into consideration intra-operative soft tissue constraints, such as ligament balance (804). Optimization parameters may include, but are not limited to: minimizing bone-implant interface stresses, reducing stress-shielding and/or implant subsidence, minimizing quadriceps and hamstring co-contraction, minimizing quadriceps forces required for various activities, achieving a natural screw-home position, reducing stress on posterior knee tissues, reducing shear loads and stresses on the patella-bone interface, matching EMG patterns of individuals with normal joint function and normal biomechanic function, achieving normal kinematics, and achieving proper ligament tension and constraint for one or more of the ACL, PCL, MCL, and LCL.

The methods provided by the present invention may be advantageously used as preoperative planning tools for determining optimal alignment and positioning of all types of prosthetic components and may even be used to construct patient-specific cutting guides and instruments (e.g., saw blade cutting blocks, drill guide blocks, router guide blocks, and mill guide blocks). In other words, after iteratively running a body simulation of a patient's knee (or other joint)

with slightly different sizes and/or spatial orientations of a particular orthopedic implant during each iteration, and after determining which spatial orientation(s) and/or sizes of said orthopedic implant provides the best overall prosthesis performance value (814), one or more patient-specific cutting guide devices may be produced from the modeling software and/or patient scans. The patient-specific cutting guide devices may be rapid-manufactured (e.g., via selective laser sintering (SLS)) and generally serve to guide a surgeon's resections, cuts, and holes in order to position the implant on the patient in the same spatial orientation which provides said best overall prosthesis performance value (814). The patient-specific cutting guide devices described herein may comprise cutting blocks that preferably have at least one B-spline 3D surface portion, or at least three strategically positioned contact points that conform to a bony or cartilaginous articulating or non-articulating surface of the individual patient's joint. The B-spline 3D surface portion or the at least three strategically positioned contact points spatially orient the block in all six degrees of freedom relative to the patient's bony anatomy in such a way that the bony resections facilitated by said patient-specific cutting guide devices effectively position one or more implants in the same optimal spatial orientation (relative to said patient's bony anatomy) suggested by the modeling software.

The virtual patient testbed described herein may be used in much the same manner as the KneeSIM Oxford rig model is conventionally used to design implant geometries. Many simulations can be run in a validated model to customize and optimize the spatial orientation(s) of a designated implant for a particular patient. Optimization is achieved by iteratively varying many different input variables and parameters in the model, running the model, recording the results, compiling the results after a predetermined number of model iterations is completed, processing the results, comparing the results, and then selecting the result or results that provide desired or acceptable overall performance. Once models are validated for different patient activities (e.g., climbing, biking, hiking, golf, walking, kneeling, etc.), they may be re-used for different patients by simply changing input parameters based on a patient's anthropometric functional characterization and/or anatomic blueprint.

Figure 2:
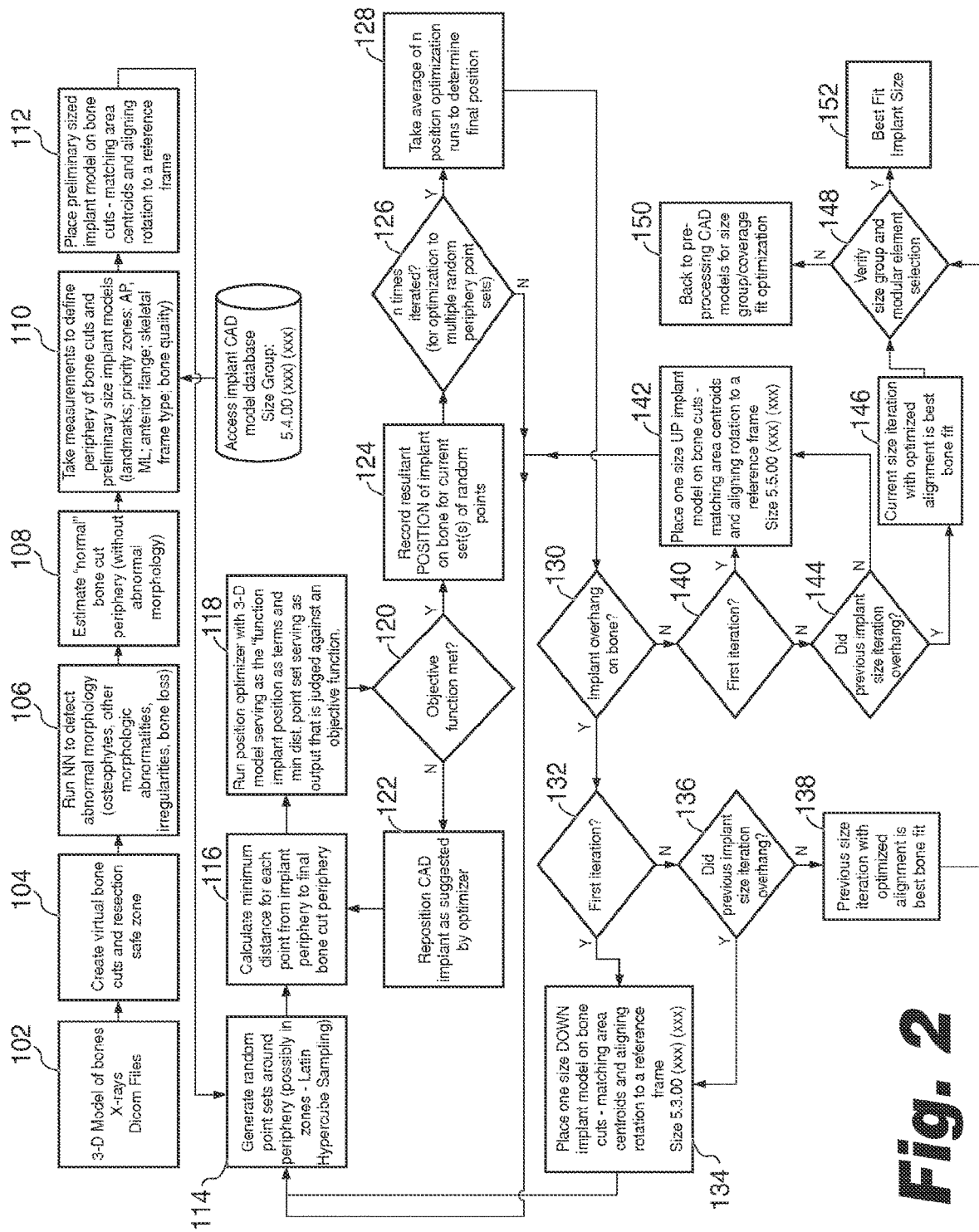
FIG. 2 schematically illustrates one non-limiting example of a method for optimizing fit of an implant to anatomy.

FIG. 2 illustrates one non-limiting example of an algorithm for optimizing the fit of an orthopaedic implant relative to a particular individual's anatomy. In the embodiment of FIG. 2, the algorithm facilitates determining the optimal position and size of a tibial implant for covering a planned resection on a patient's proximal tibia. Those of skill in the art will recognize that this or similar algorithms could be used to optimize the fit (e.g., in terms of position and size) of other implants for other orthopaedic procedures, including, without limitation, other knee implants (e.g., femoral or patellar), hip implants, shoulder implants, or implants for other joints or anatomy. It should be understood that the usefulness of the present invention is not limited to total knee arthroplasty (TKA) applications. Rather the methods of the present invention may serve as well in knee hemi-arthroplasty, knee resurfacing, knee uni-compartmental arthroplasty, knee bi-compartmental arthroplasty, total hip arthroplasty (THA), hip hemi-arthroplasty, hip resurfacing, shoulder arthroplasty, shoulder hemi-arthroplasty, elbow reconstruction, ankle reconstruction, and other surgical applications.

The method of FIG. 2 may be generally divided into pre-processing of bone CAD models for size group/coverage fit optimization (steps 102-108), position optimization (steps 110-128), size optimization (steps 130-146) and verification (steps 148-152). Although specific examples of steps for performing those processes are set forth below, those of skill in the art will recognize that other process steps may substitute for or otherwise alter the specific, non-limiting examples provided below.

Pre-Processing

The first step 102 in FIG. 2 is the creation of a three-dimensional anatomic model of the patient's anatomy. The three-dimensional anatomic model may be created by segmenting or otherwise processing imaging data of the patient's anatomy, such as MRI, CT, x-ray, ultrasound, or other imaging data, to reconstruct the exact geometry and shape, or otherwise define the relevant surfaces and other morphological aspects of the patient's anatomy. Such segmenting may be accomplished by manual, automated, or semi-automated processes. In some embodiments, segmentation may be facilitated by software packages available from, for instance, Able Software Corp. of Lexington, Massachusetts (3D-doctor), Materialise of Leuven, Belgium (Mimics) or other software. Segmenting or other processes may identify bony surfaces of the anatomy, surrounding soft tissue and cartilage surfaces of the anatomy, bone-cartilage interfaces, or other biological features or relevant portions of the anatomy.

The imaging data or other information concerning the patient also may be used to identify additional qualitative or quantitative information for incorporation into or other use with the three-dimensional anatomic model, such as, but not limited to, a position and/or orientation of the mechanical axis of the patient's leg relative to the three-dimensional anatomic model and other reference frame information (e.g., identification of particular reference points, axes or other constructs with respect to the three-dimensional anatomic model). The three-dimensional model also may incorporate or otherwise reflect information relating to mechanical properties of bone (e.g., bone quality), cartilage and soft tissues.

Figure 3:
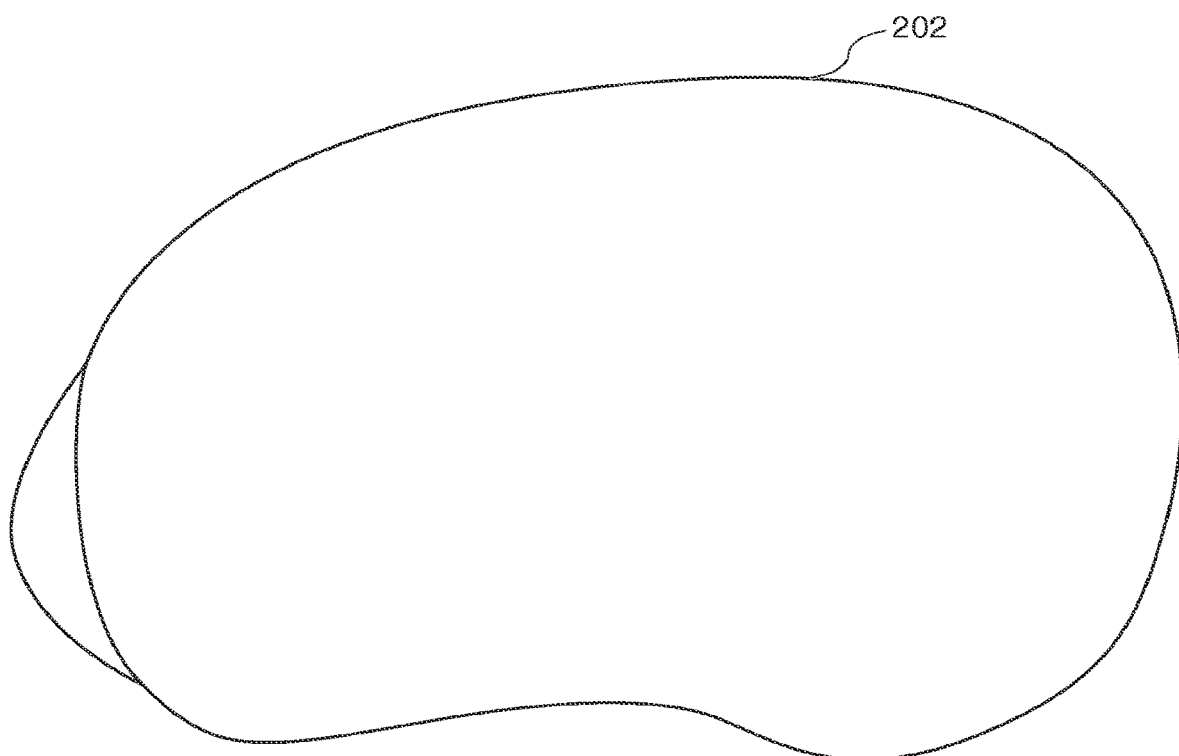
FIG. 3-15 schematically illustrate certain steps in the method of FIG. 2.
Figure 4:
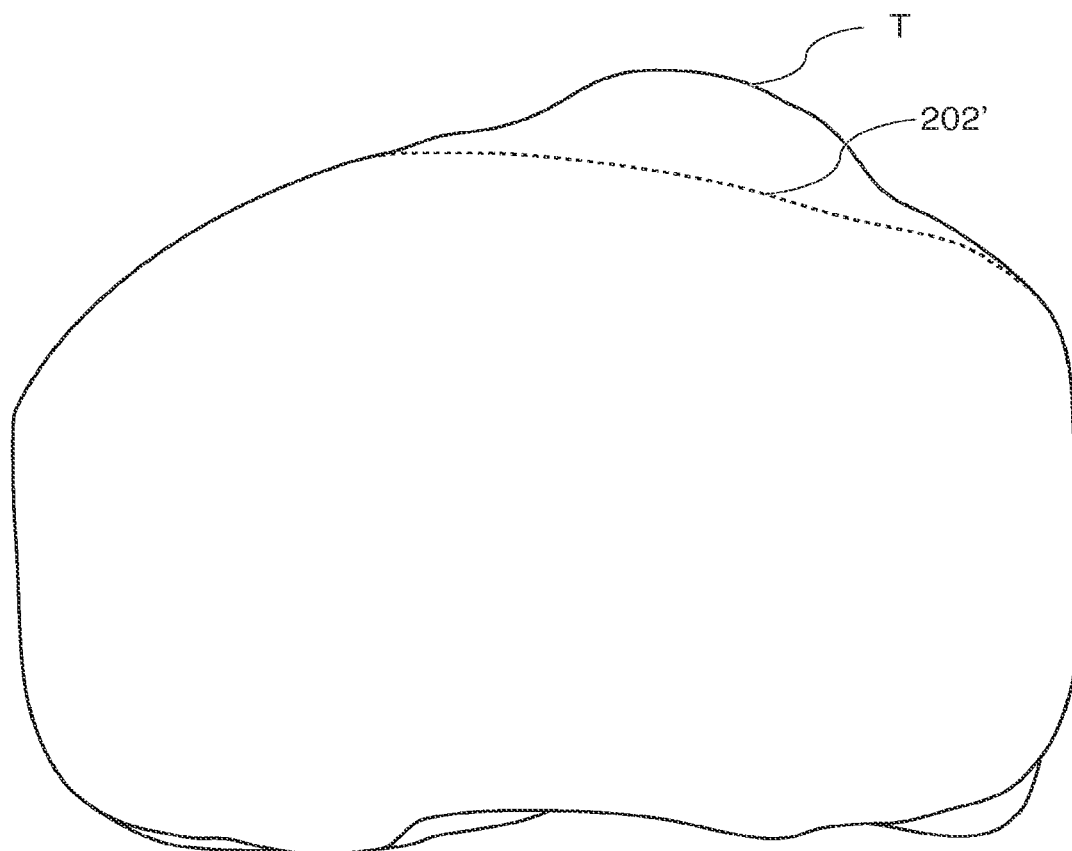

The next step 104 in the algorithm of FIG. 2 is the creation of a virtual resection or resections on the anatomic model. Alternatively, an "implant pose" may be computed. In this particular embodiment, the virtual resection may reflect a planar resection to the proximal tibia creating a planar surface for receipt of a tibial implant (such as a tibial baseplate). FIG. 3 shows a top plan view of the planar surface of the resected tibial model and its outer periphery 202. FIG. 4 shows the outer periphery 202' of the planned resection relative to the three-dimensional model of the un-resected tibia T. In other embodiments, multiple resections may be defined in the anatomic model. For instance, in one example involving a model of the femur, distal, anterior, posterior, anterior chamfer and posterior chamfer resections may be defined. The resection or resections may be defined in the anatomic model using a wide variety of automated, semi-automated and manual techniques. Of course in the case of partial knee arthroplasty or hemiarthroplasty, the outer periphery would be truncated so as to not include the entire resection surface. For example, the resection, an thus the outer periphery, may be truncated along a portion of the tibial eminence.

Any of the disclosure above regarding biomechanical fit may be used to generate one or more additional design inputs to the virtual resection model 104.

In some embodiments, the anatomic model may include multiple bones (e.g., a femur and tibia), and resections may be defined in those bones using a variety of techniques. In one embodiment, a measured resection approach may be utilized in which the resections in the femur are determined independently of the resections in the tibia. For instance, femoral resections may be determined from measurements or other references to features on the femur (e.g., distal most point of a medial or lateral condyle, distal point of a patello-femoral groove, etc.), while tibial resections may be determined from measurements or other references to features on the tibia (e.g., features on a tibial plateau), independent of the spatial relationship between the femur and the tibia. In other embodiments, techniques may be utilized in which the resections on one bone are determined in whole or part by reference to the opposing bone. For instance, in some embodiments, resections in the femur may be determined, in whole or in part, by reference to planned resections in the tibia or features of the un-resected tibia, or vice versa. In these embodiments, an actual or desired tension of the ligaments and/or other soft tissues associated with the joint may also be referenced in determining resection positions and/or orientations. In some embodiments, resection position and/or orientation or other aspects of the orthopaedic procedure may be determined, in whole or in part, by reference to a joint gap or joint space measurement between two anatomic structures such as bones, which may be carried out, for example, using virtual measurement tool equivalents of spacer sets, tensors, or other devices that will be familiar to those of skill in the art.

In various embodiments, manual, semi-automatic and fully automatic techniques may be utilized to define resections to the anatomic model. In some manual embodiments, surgeon input, surgeon preferences, or input by other users may be used to define resection planes in the anatomic model in manners similar to techniques used with traditional arthroplasty procedures. In other embodiments, position and orientation of the resection planes may be based on computer implemented algorithms designed to optimize biomechanic performance and other aspects of the arthroplasty procedure.

Figure 5:
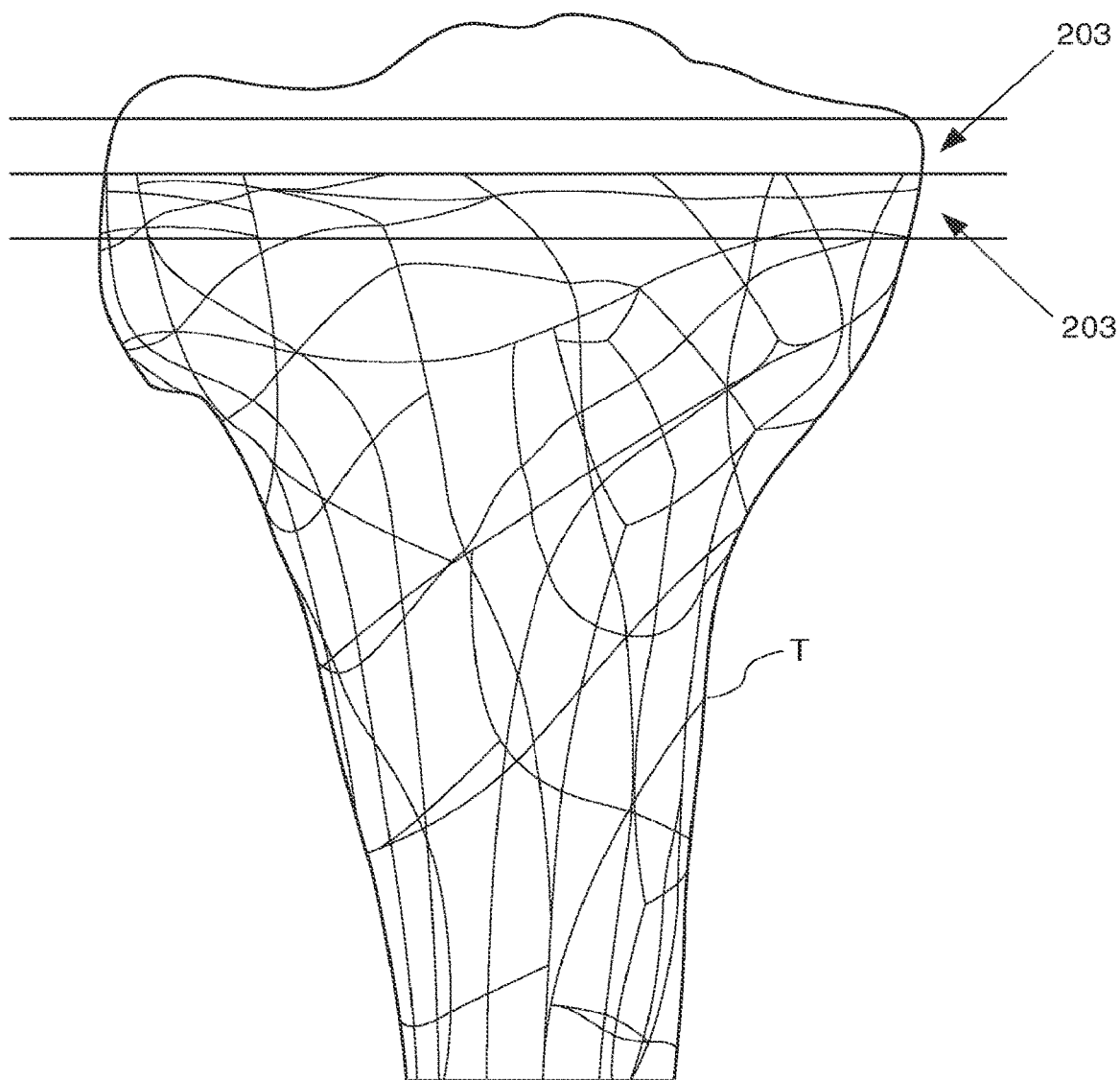

In the particular embodiment shown, a resection safe zone 203 also is determined in step 104 for the resection(s). In some embodiments, the resection safe zone 203 encompasses areas approximately 1-2 mm superior and inferior the planned resection. In some embodiments, the safe zone may be used as a guide for a safe resection, for a less or more aggressive bone cut. FIG. 5 illustrates one non-limiting example of the safe zones 203 surrounding a planned resection to a proximal tibia. Alternatively, the resection safe zone may be based upon manufacturing tolerances, instrumentation variability, and/or allowance for errors in medical imaging.

Figure 6:
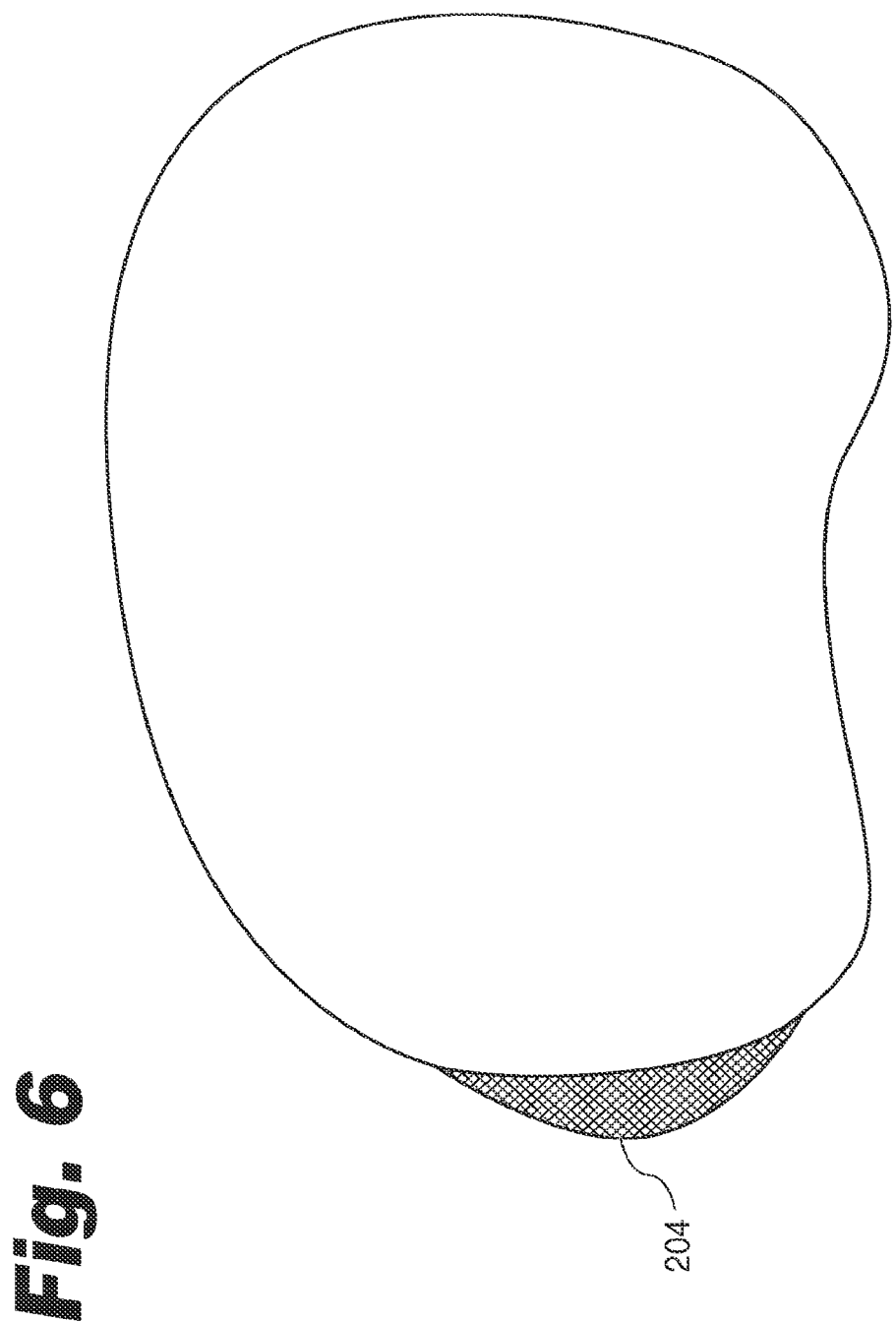

In the non-limiting example of FIG. 2, the next step 106 is detection of abnormal morphology. Abnormal morphology may include, without limitation, osteophytes or other morphologic abnormalities, irregularities, or areas of bone loss. FIG. 6 shows an area of an osteophyte 204 identified in this step 106. In the embodiment of FIG. 2, a trained neural network is used to identify abnormal morphology on the resected three dimensional model, although other automated, semi-automated or manual techniques could be used. For instance, in other embodiments, automatic segmentation processes may allow identification of abnormal morphology (using, for instance, threshold based, probabilistic atlas based, statistical shape modeling based, or other techniques). Some embodiments may at least partially utilize Matlab based processes (of MathWorks, Inc., Natick, MA) as part of such processes. In some embodiments, the user and/or surgeon has the option of simulating various amounts of osteophyte removal. Depending upon surgeon preference, a specified amount of bone removal may be substituted for the recommended amount from the simulation as osteophytes mostly affect ligament wrapping.

Figure 7:
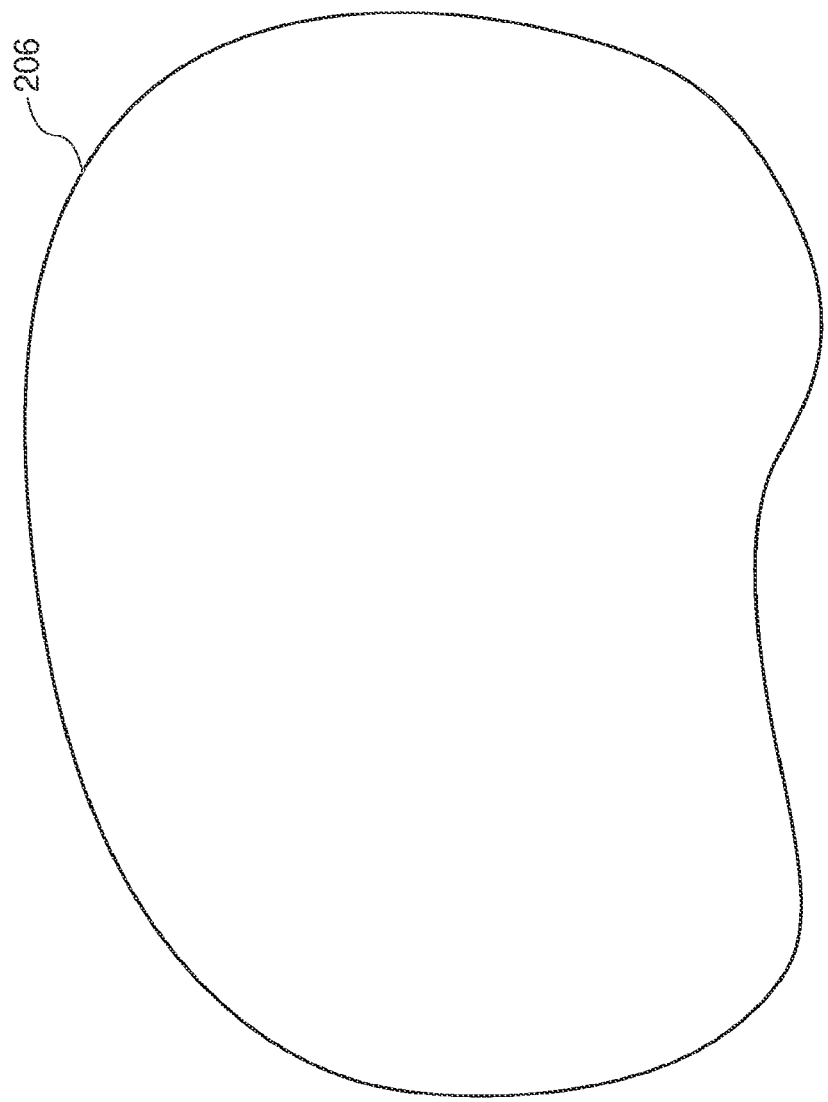

As shown in FIG. 2, once any abnormal morphology has been identified on the resected three dimensional model, the next step 108 is an estimation of the periphery of the resected three dimensional model without the abnormal morphology. FIG. 7 shows an estimation of the periphery 206 without the abnormal morphology, such as the osteophyte 204.

Position Optimization

The position optimization steps of FIG. 2 begin with step 110, which identifies a preliminary size for the implant component for use on the resected surface. In this particular embodiment, measurements in one or more medial-lateral and anterior-posterior dimensions are made based on the estimated periphery 206 and the preliminary implant size is selected from a database of possible implant sizes. In some instances, the database may include CAD or other computer three-dimensional models of the different sizes of implants. In some embodiments, there may be hundreds or thousands of possible implant sizes.

As noted above, the patient-specific cutting guide devices described herein may comprise cutting blocks that preferably have at least one B-spline 3D surface portion, or at least three strategically positioned contact points that conform to a bony or cartilaginous articulating or non-articulating surface of the individual patient's joint. The B-spline 3D surface portion or the at least three strategically positioned contact points spatially orient the block in all six degrees of freedom relative to the patient's bony anatomy in such a way that the bony resections facilitated by said patient-specific cutting guide devices effectively position one or more implants in the same optimal spatial orientation (relative to said patient's bony anatomy) suggested by the modeling software. In some embodiments, the system may include a library of 2D or 3D B-splines for comparison or matching to patient B-splines.

Figure 8:
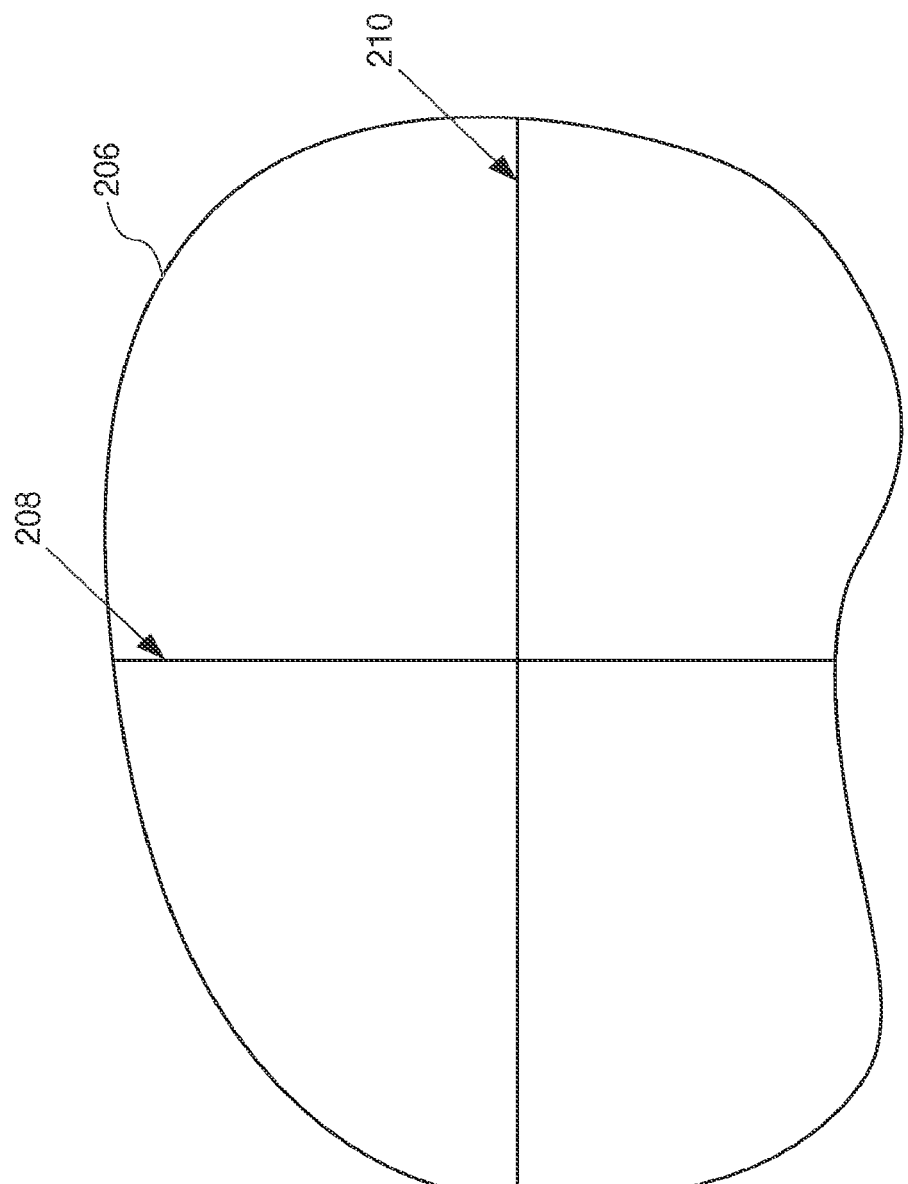

FIG. 8 illustrates non-limiting examples of anterior-posterior 208 and medial-lateral 210 measurements that may be made relative to the periphery 206 on the resected three dimensional anatomic model. In other embodiments, multiple medial-lateral, multiple anterior-posterior, and/or other measurements in other dimensions may be made. These measurements may be used to initially select an implant model from the database of implant models that most closely approximates the measured dimensions.

Figure 9:
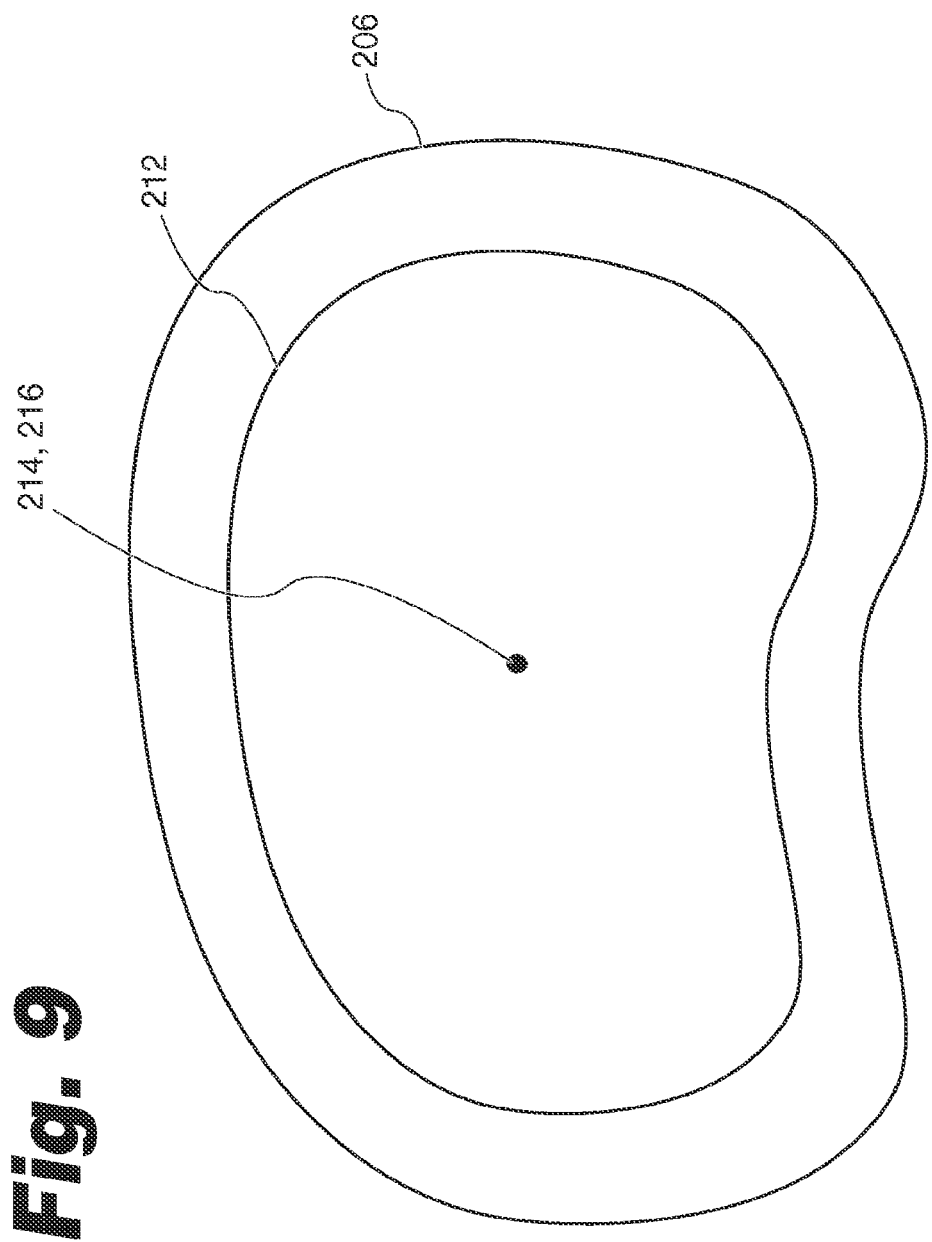

The next step 112 shown in FIG. 2 is to initially position the preliminarily selected implant model relative to the three-dimensional bone cut model. In this example, the initial positioning is performed by aligning the centroid of the CAD implant model with the centroid of the resected bone surface of the three-dimensional bone cut model. Initial positioning and alignment of the implant model relative to the resected anatomic model may involve aligning the reference frames of the implant and resected anatomic models with respect to one another using fixed skeletal landmarks, such as alignment based off of the tibial tubercle. FIG. 9 illustrates the periphery 212 of the preliminarily selected implant model positioned relative to the periphery 206 of the resected anatomic model, with the centroids 214, 216 of the models aligned. Alternatively, the preliminary selected implant model perimeter could be determined by fitting a polynomial curve to the resected bone and making a best-fit comparison to the spline library.

Figure 10:
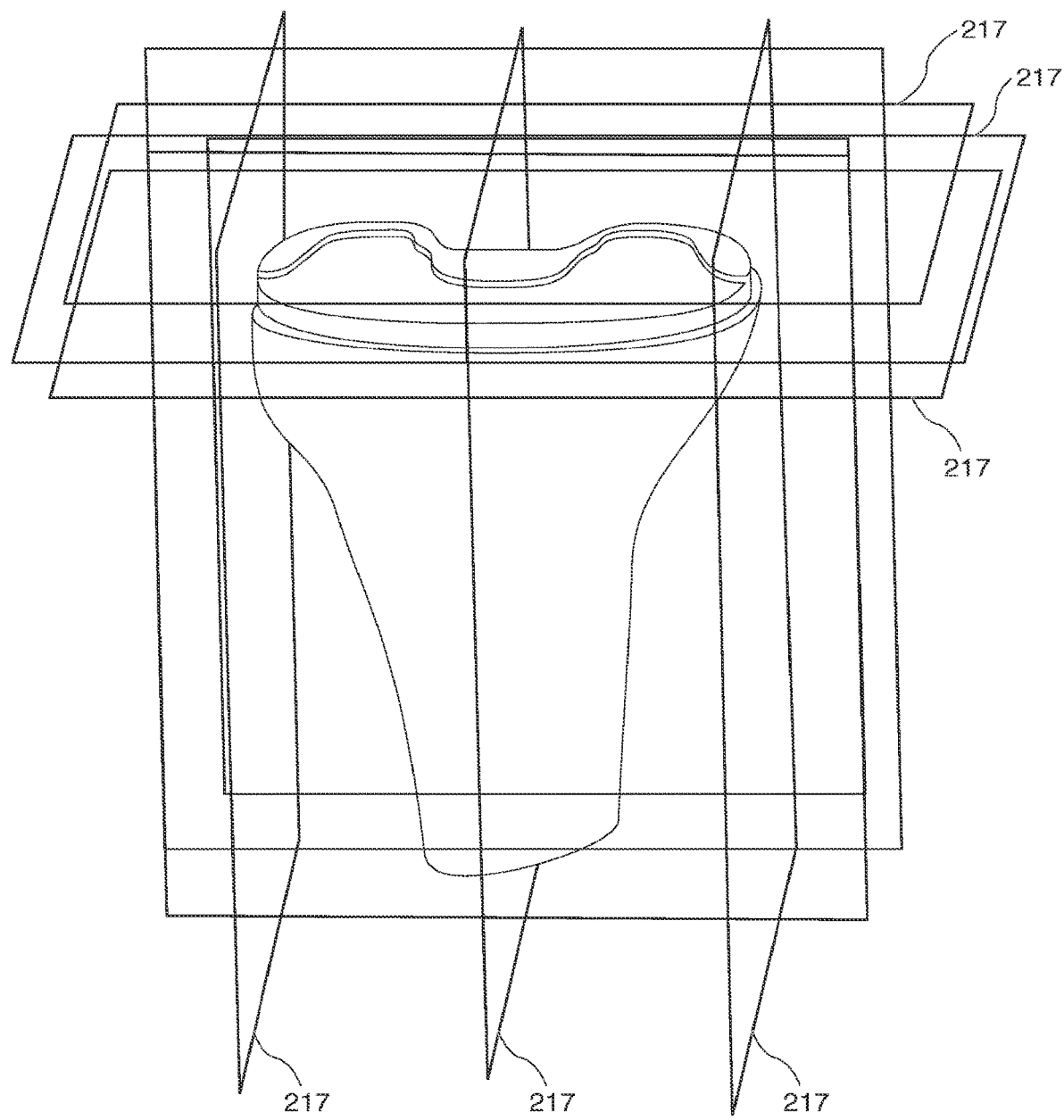

In other embodiments, techniques other than centroid alignment could be used to initially position the implant model relative to the anatomic model. For instance, in some embodiments, various axes of the anatomic model (anatomic axes, mechanical axes, anterior-posterior axis, epicondylar axis) could be aligned relative to axes, other features or constructs associated with the implant model. FIG. 10 illustrates non-limiting examples of various planes and/or layers 217 of a resected tibial and implant model that may be used for the initial alignment. In some embodiments, skeletal landmarks (e.g. tibial tubercle, condyles, etc.) may be used in addition to or instead of any of the above. In some embodiments, a center of medial-lateral and anterior-posterior dimensions of the models may be used for alignment (or a fixed offset from such centers). In some embodiments, centers or other aspects of circles (e.g., perimeter, arches, radii, diameters, etc.) circumscribing the models could be employed for alignment.

Figure 11:
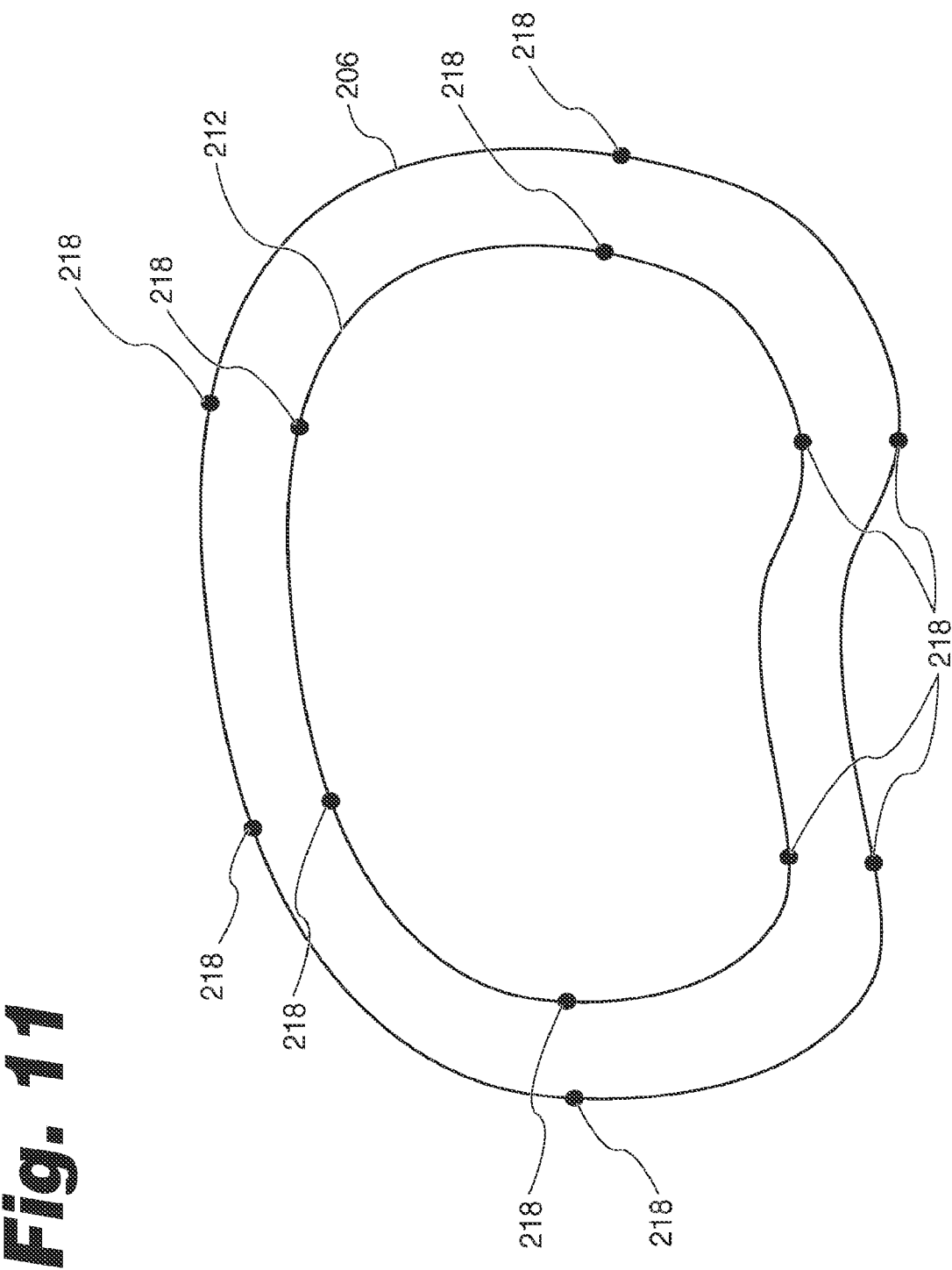
Figure 12:
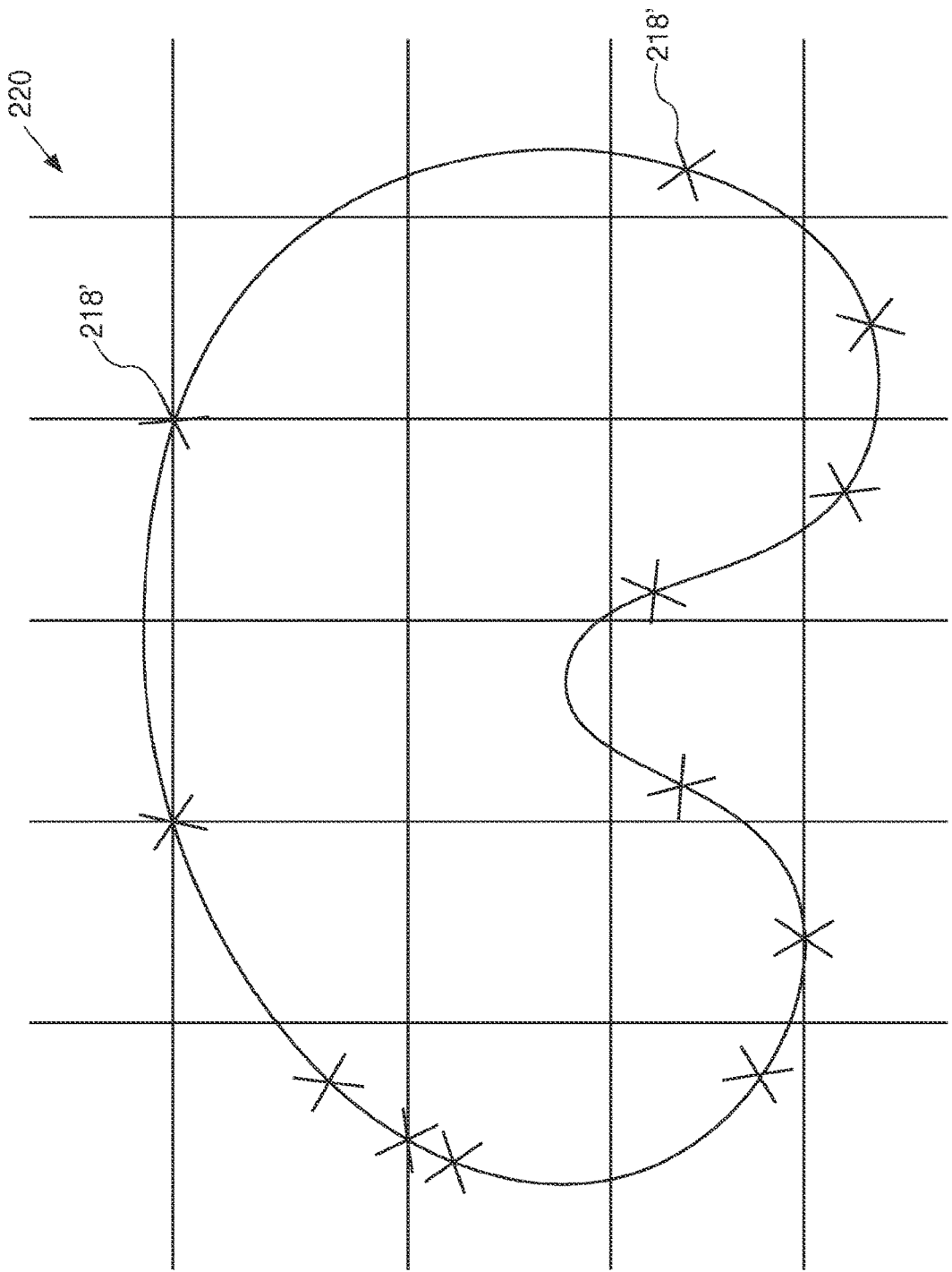
Figure 13:
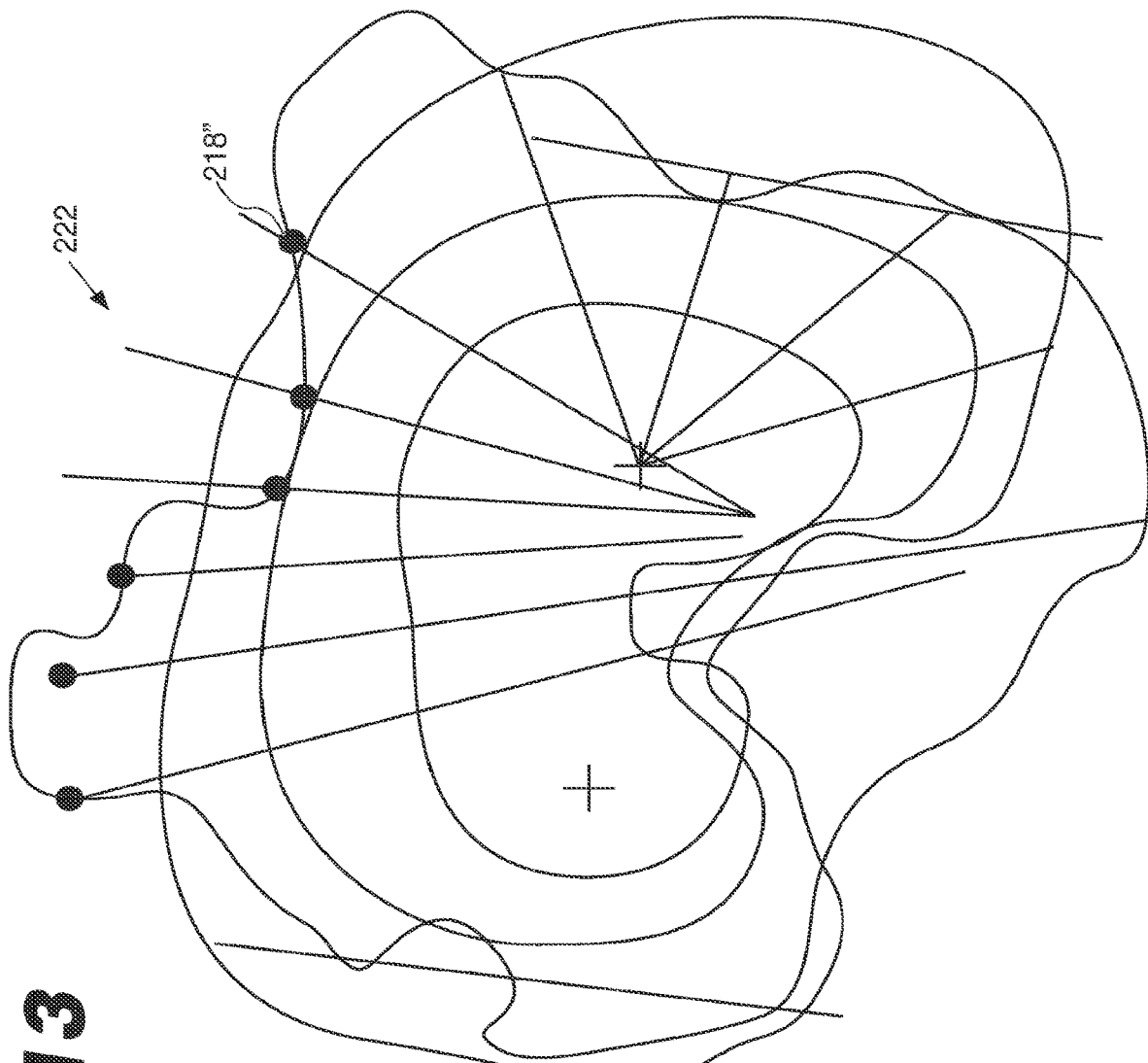

In the particular example of FIG. 2, the next step 114 is the generation of random point sets around the peripheries of the anatomic and implant models. FIG. 11 shows one example of randomly generated point sets 218. In this particular embodiment, the point sets are generated randomly using statistical techniques, such as Latin Hypercube Sampling, although, in other embodiments, other statistical, random or non-random techniques may be used. In some embodiments, priority zones may be utilized (e.g., anterior region, posterior region, medial region, etc.) instead of or in addition to randomly identifying points around the perimeter. In some embodiments, a grid system 220 such as shown in FIG. 12 may facilitate identifying point sets 218'. In other embodiments, a radial distribution 222 such as shown in FIG. 13 may be used. In such embodiments, points 218" may be initially identified on one of the resected anatomy and implant models and corresponding points identified on the other of the anatomy and implant models using such a grid or radial technique. Some embodiments may utilize random points whereas other embodiments may utilize uniformly distributed points. For example, the "control points" of cross-section splines could be used with the number and location of points being related to the amount of curvature in the line. Further, there may be a minimum set of control points as extra points do provide much influence in the way of shaping the bone. In some embodiments, more points are located in areas of high curvature and less points are located in areas of low curvature. In some embodiments, larger models may utilize more points than smaller models.

Figure 14:
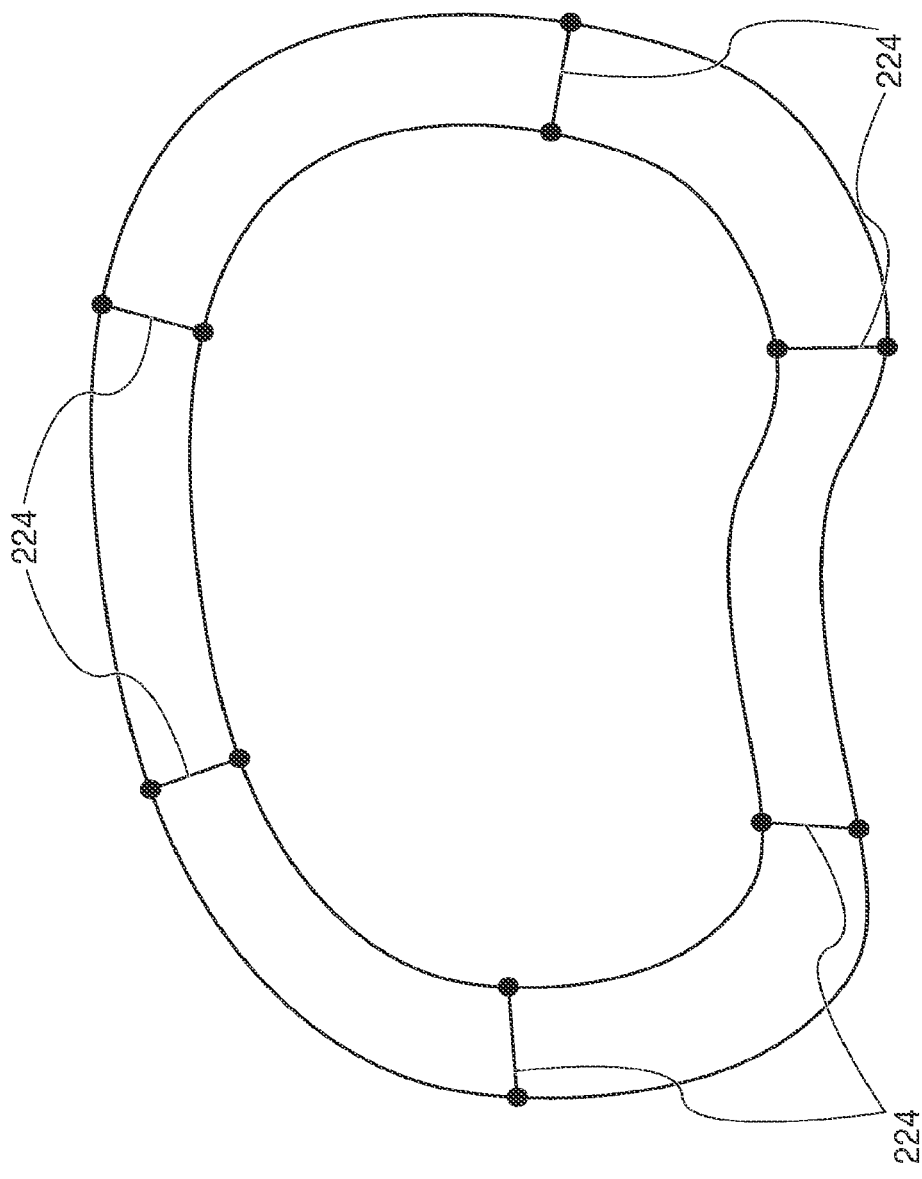

In the next step 116, minimum distances between the point sets are calculated. These distances 224 are schematically illustrated in FIG. 14. In other embodiments, techniques other than measuring minimum distances between point sets could be used. For instance, in some embodiments, the area difference between the cross-sections of the two models may be calculated. In these or other embodiments, the area difference may be used to calculate its centroid and the distance between corresponding points. In some embodiments, a virtual spring or springs based algorithm may be applied to the models to determine an equilibrium position of the implant model on the resected surface of the anatomic model.

In the next steps 118 and 120, a position optimizer is used to determine whether the current positioning of the selected implant periphery relative to the anatomic periphery is optimal. In some embodiments, the position optimizer utilizes a computer algorithm based on, for example, mathematical expressions to identify the minimum distance between two points, a functional relationship incorporating data about the anatomic periphery and location (and possibly other aspects of the anatomic model), the implant periphery and location, and minimum distance point sets to judge whether the current positioning of the selected implant relative to the anatomic model meets an objective function. If it does not, in step 122, the position of the selected implant model is incrementally translated relative to the anatomic model and steps 116-120 are repeated.

In the embodiment of FIG. 2, if the objective function is determined to be met, the algorithm proceeds to step 124 in which the current position of the selected implant relative to the anatomic model is recorded. In step 126, the algorithm determines whether steps 114-124 have been iterated a suitable number of times (e.g. more than once). If not, the algorithm returns to step 114 to generate random point sets again and repeat the position optimization steps. If steps 114-124 have been iterated a suitable number of times, the algorithm proceeds to step 128 in which an average optimized position is determined from the previous iterations. In other embodiments, step 126 is not necessary and the method only requires a single iteration of the position optimization steps. Data concerning the averaged optimized position and selected implant are used in the steps described below relating to optimization of implant size.

One of skill in the art will recognize that other processes than the one illustrated by steps 114-128 may be utilized to determine an optimal position for the implant model relative to the anatomic model.

Size Optimization

In the example of FIG. 2, beginning with the initially selected implant model and average optimized position determined by steps 110-128, steps 130-146 progress through the possible sizes of implant models to identify the size providing the best coverage of the resected anatomy without overhang.

Figure 15:
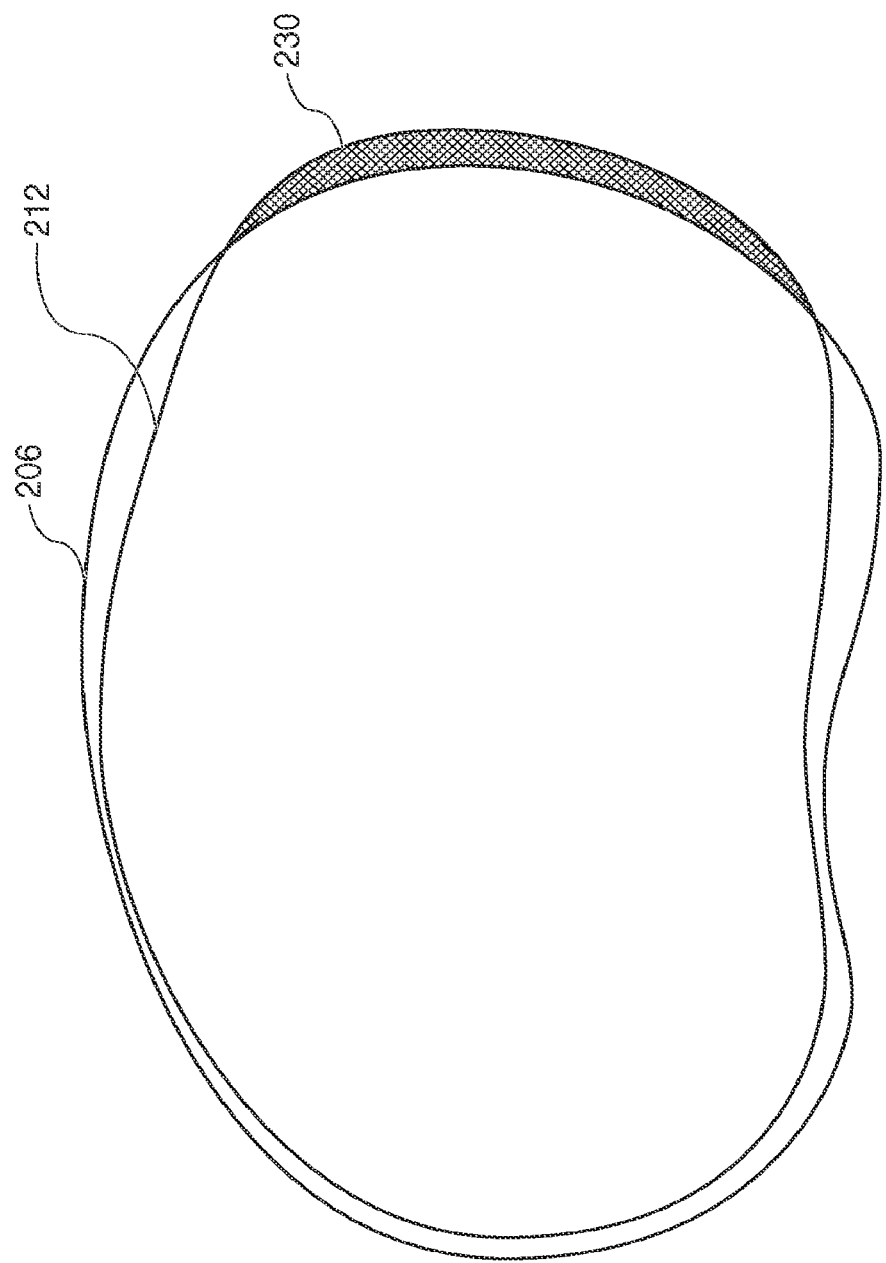
Figure 16:
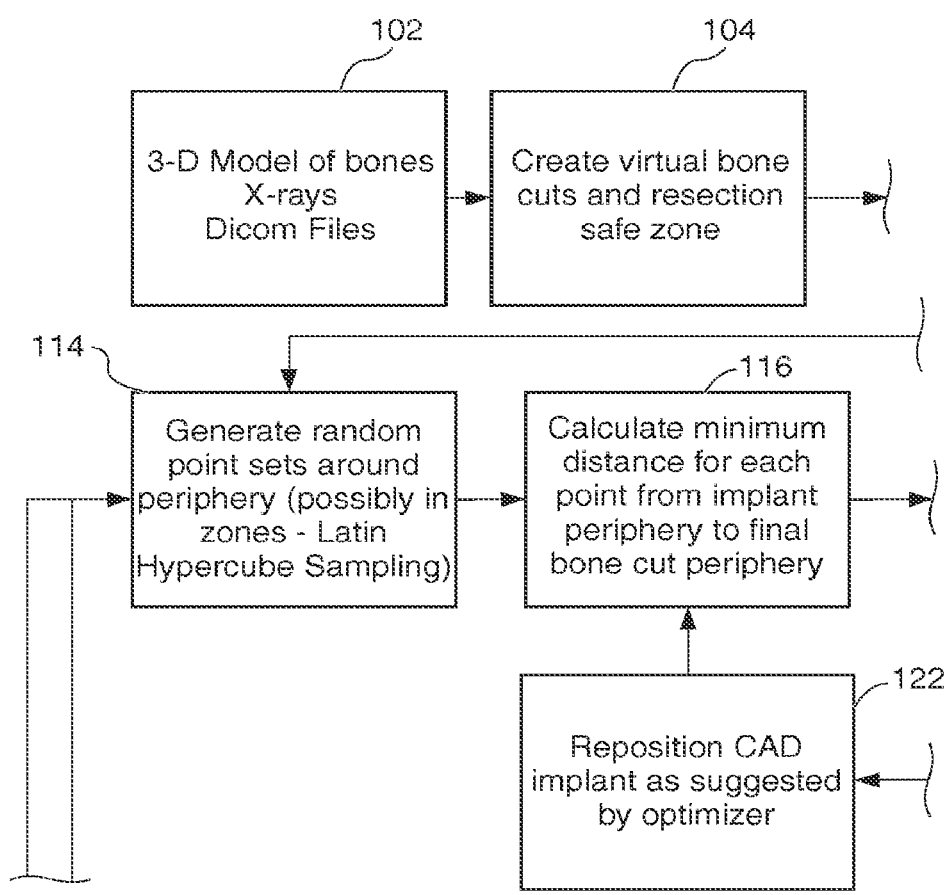
FIGS. 16-21 are enlarged portions of the method of FIG. 2.
Figure 17:
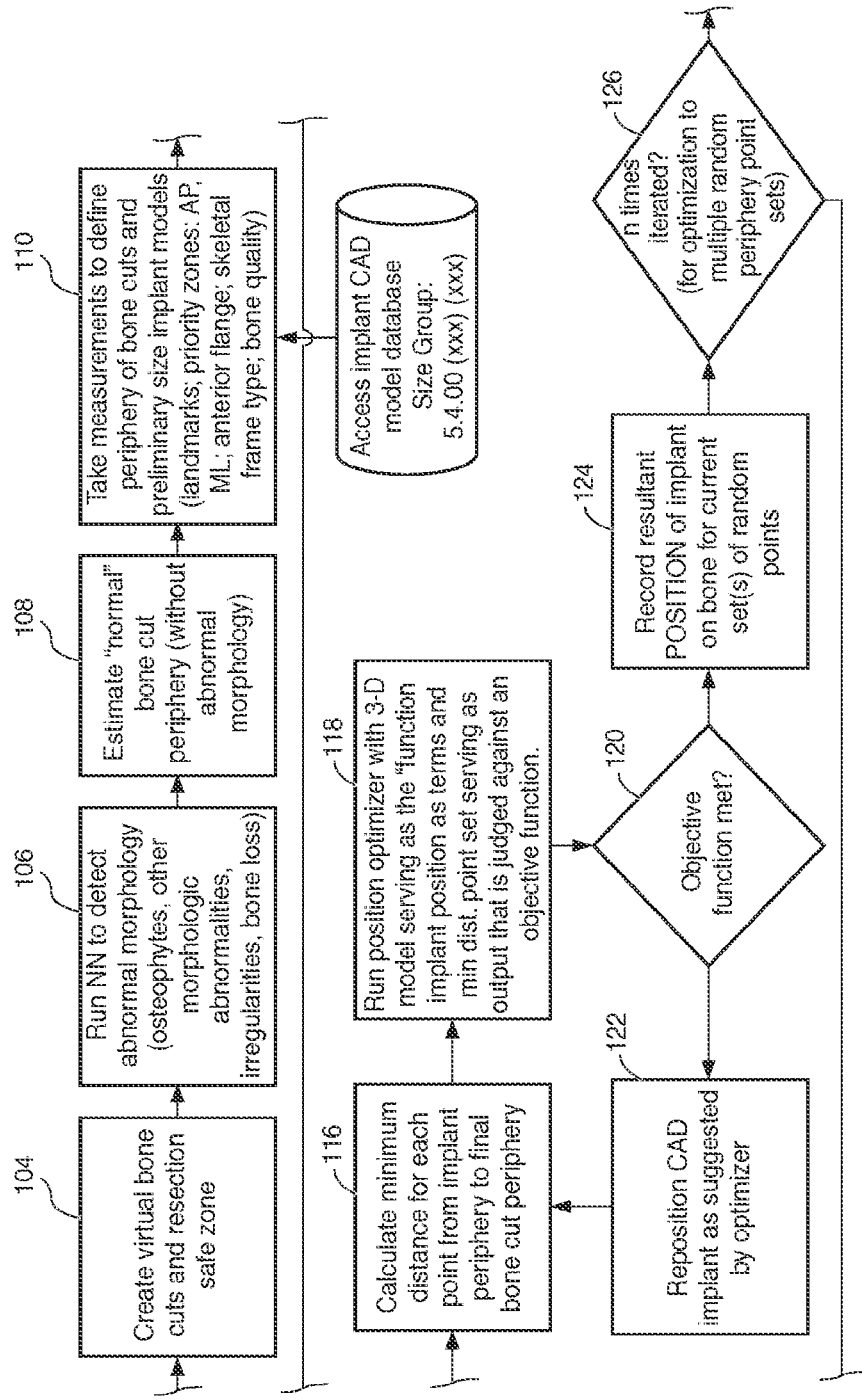
Figure 18:
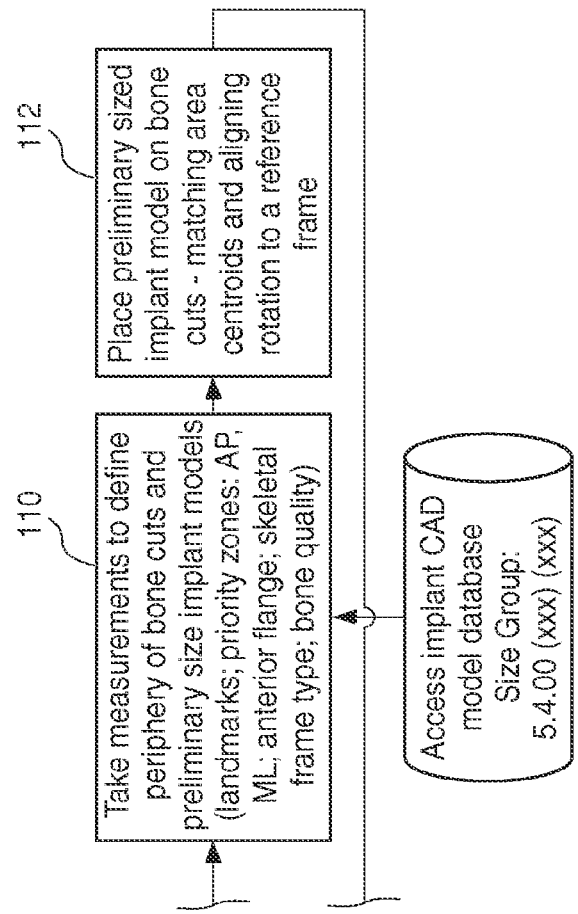
Figure 19:
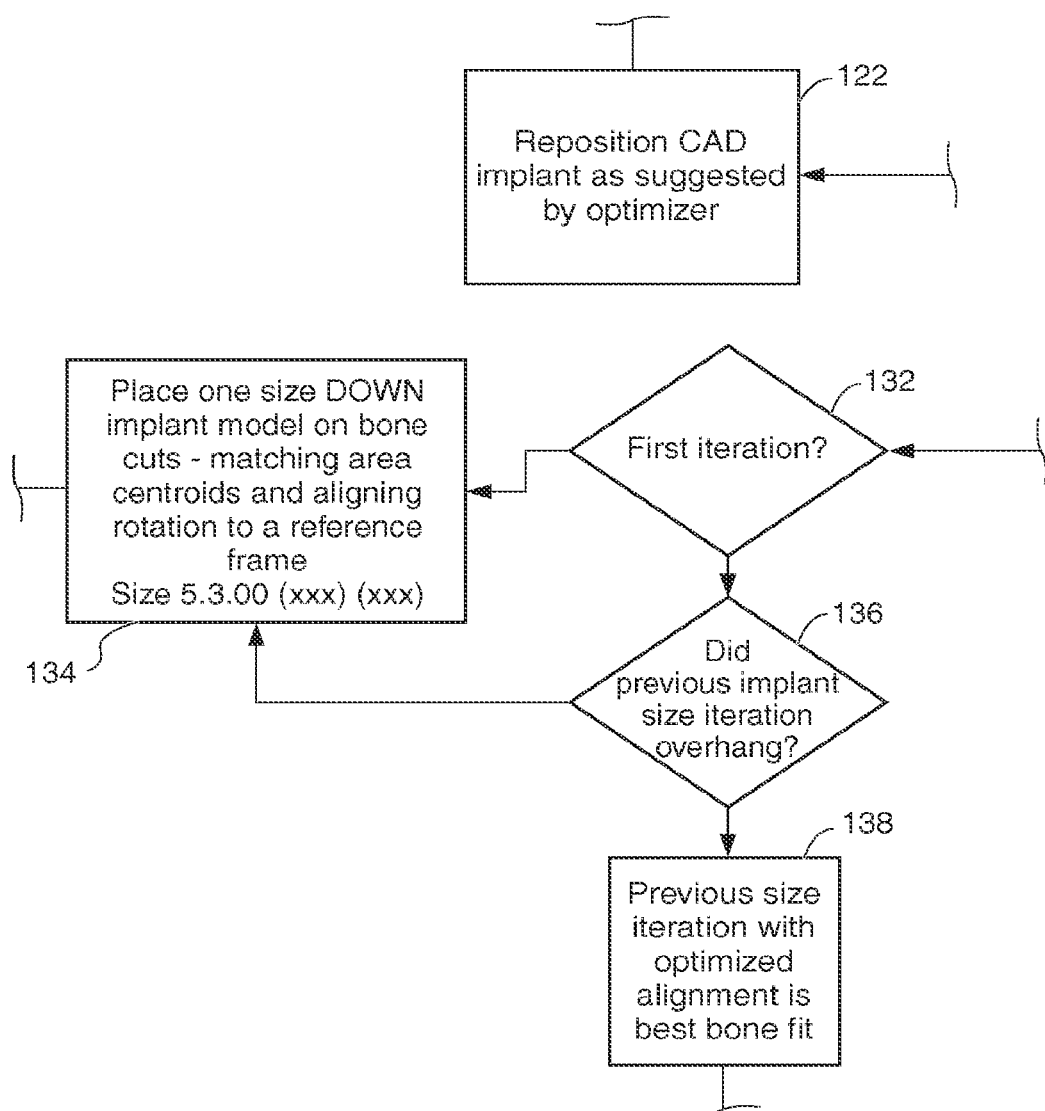
Figure 20:
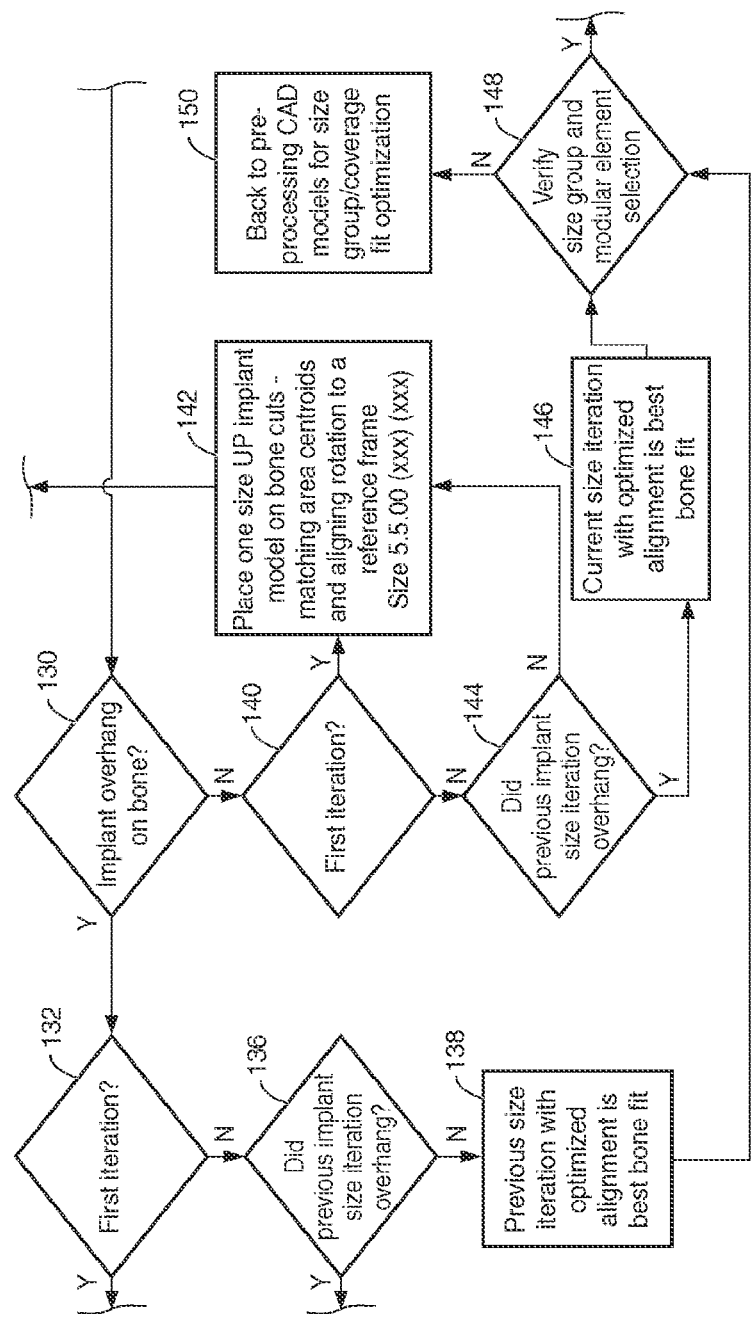
Figure 21:
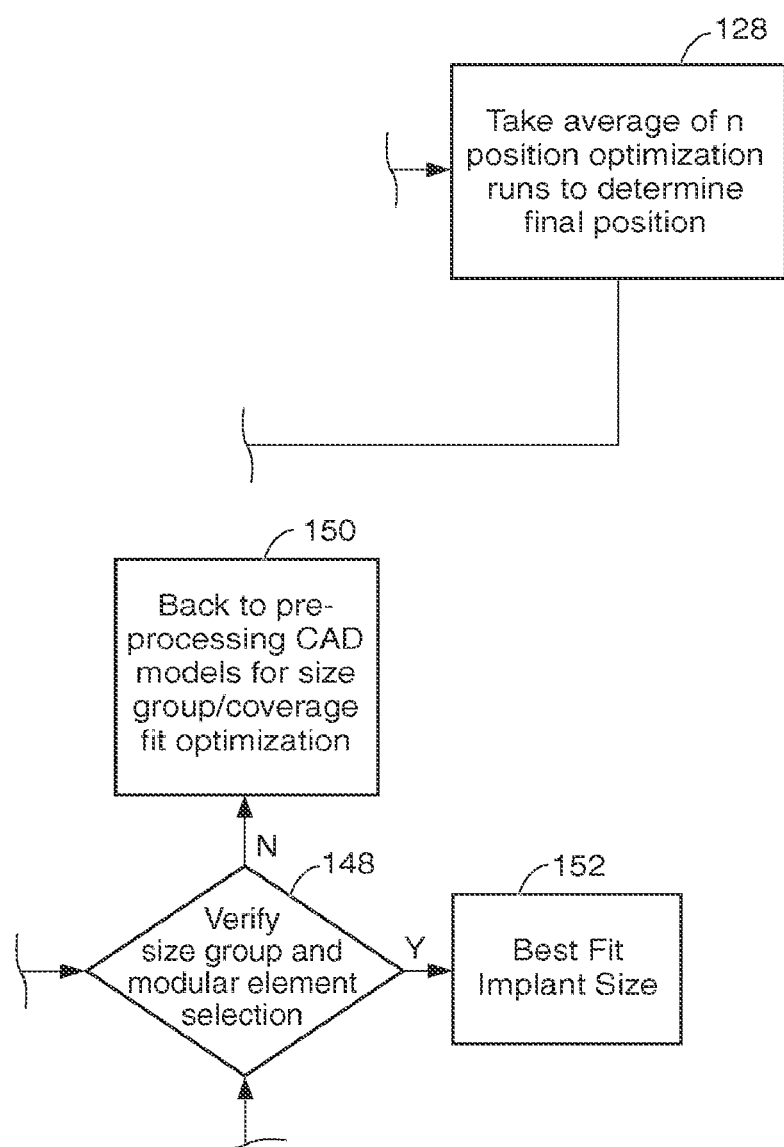

In step 130, it is determined whether the selected implant model (when positioned at the optimized position or average optimized position) would result in overhang. FIG. 15 schematically illustrates one non-limiting example of overhang 230 between the selected implant's periphery 212 and the anatomic model periphery 206. In the embodiment shown, if it is determined at step 130 that there is overhang, the process proceeds to step 132, in which it is determined whether this is the first iteration through the size optimization steps. If so, in step 134, the next size "down" implant model is selected and is used in a further iteration of the position optimization (steps 114-128) and size optimization (steps 130-146) procedures. One of ordinary skill in the art will recognize that moving a size "down" does not necessarily require that the next implant model be smaller in some or all dimensions than the previous implant model analyzed. In some instances, moving a size "down" may reflect a decrease in some dimensions of the implant model (e.g., medial-lateral width) while other dimensions remain the same between the particular sizes (e.g., anterior-posterior width). In some instances, moving a size "down" may not always require a decrease in a particular dimension, but could reflect a change of shape in, for instance, the implant models' peripheries. Similar concepts are associated with moving "up" a size, which is discussed in further detail below. In some embodiments, there is an ordered hierarchy to the possible implant sizes along which "up" and "down" sizes can be selected (e.g., 5.1, 5.2, 5.3, 5.4, etc.).

Returning to step 132, if it is not the first iteration through the size optimization steps, the method proceeds to step 136, in which it is determined whether the previous iteration through the size optimization steps identified overhang for that implant model. If overhang was not identified in the previous iteration, the method proceeds to step 138, in which the implant model analyzed in the previous iteration (along with its optimized position) that did not result in overhang is identified as the best fit for the patient's particular anatomy. If at step 136 it is determined that the previous iteration did result in overhang, the method proceeds to step 134 discussed above, in which the next size down implant model is selected for further analysis.

Returning to step 130, if it is determined that the currently selected implant model does not result in overhang, the method proceeds to step 140, in which it is determined if this is the first iteration through the size optimization steps. If, at step 140, it is the first iteration through the size optimization steps, the method proceeds to step 142, the next size "up" implant model is selected and is used in a further iteration of the position optimization (steps 114-128) and size optimization (steps 130-146) procedures. If, at step 140, it is not the first iteration through the size optimization steps, the method proceeds to step 144, in which it is determined whether the previous implant model size iteration resulted in overhang. If not, the method proceeds to step 142, selecting the next size up implant model for further analysis. If so, the method proceeds to step 146, in which it is determined that the current size implant model is identified as the best fit for the patient's particular anatomy.

Verification

The non-limiting example illustrated in FIG. 2 includes verification steps 148-152 in which various aspects of the planned orthopaedic procedure can be verified, either by a user (such as an engineer, doctor, or other user) or by a semi or fully automated verification procedure. In the particular embodiment illustrated, at step 148, information is outputted to a user sufficient to verify that the optimal implant size and position identified appears to be correct and that such identified implant size is appropriate for other components used for the surgical procedure (e.g. that an identified tibial implant is suitable for use with a particular femoral implant). In step 148, if the user verifies the outputted information, the process outputs information at step 152 for use in subsequent procedures, such as information sufficient to manufacture patient-specific implants and/or instrumentation. There may be more than one best-fit implant size outputted. The system may provide, as an example, 5 best fit options. If the user does not verify the outputted information in step 148, as shown by step 150, the process may return to earlier steps of pre-processing, position optimization, and/or size optimization.

In some embodiments, an engineer may review and verify a pre-operative plan including details about the proposed surgical procedure, such as the bone model, measurements, planned resections, images, proposed placement of the implant relative to the bone model, etc.). In some embodiments, the pre-operative plan may also be sent to the surgeon for approval (by electronic mail, uploading to the internet, physical mail, or other means) or for the surgeon to propose changes to the plan. If approved, 3D CAD models and/or other information may be sent for production of instruments and/or implants for the procedure.

Computer Systems

In some embodiments, image processing, position optimization, size optimization and other steps may be carried out, wholly or at least partially, using a computing device. The computing device may be part of or remote from the device or devices used to image the patient and the device or devices used to custom manufacture instrumentation, implants or other devices for carrying out the procedure, and may receive or access data reflecting the images obtained of the patient through any appropriate communication medium, including wireline, wireless, optical, magnetic, or solid state communication mediums. The computing device may include a processor that can execute code stored on a computer-readable medium, such as a memory. The computing device may be any device that can process data and execute code that is a set of instructions to perform actions. Examples of the computing device include a database server, a web server, desktop personal computer, a laptop personal computer, a server device, a handheld computing device, a mobile device, or combinations thereof.

In some embodiments, the processor may include a microprocessor, an application-specific integrated circuit (ASIC), a state machine, or other suitable processor. The processor may include one processor or any number of processors, and may access code stored in memory. The memory may be any non-transitory computer-readable medium capable of tangibly embodying code. The memory may include electronic, magnetic, or optical devices capable of providing processor with executable code. Examples of the memory include random access memory (RAM), read-only memory (ROM), a floppy disk, compact disc, digital video device, magnetic disk, an ASIC, a configured processor, or other storage device.

In some embodiments, the computing device may share and/or receive data with additional components through an input/output (I/O) interface. The I/O interface may include a USB port, an Ethernet port, a serial bus interface, a parallel bus interface, a wireless connection interface, or any suitable interface capable of allowing data transfers between the computing device and another component. The additional components may include components such as an information database. In other embodiments, the computing device includes the information database.

Some embodiments may include a user interface, such as a web user interface, allowing engineers, surgeons, or other users to upload data such as imaging data, documents, surgeon notes, preferences, etc. The interface could be a graphical user interface allowing a user to upload, access, visualize, annotate, and/or manipulate x-rays, MRIs, DICOM files, 3D CAD models, etc. The interface, in some embodiments, may allow the user to move the bone and implant models, and suggests different position, orientation, sizes, cutting planes, etc.

One of ordinary skill in the art will recognize that additions, deletions, substitutions or other modifications may be made to the non-limiting embodiments described above without departing from the scope or spirit of the present invention.

For instance, without limitation, while the above description focuses on embodiments for optimizing fit of an implant to a resected surface on a bone, those of skill in the art will recognize that the concepts embodied herein are also applicable to orthopaedic procedures that do not involve bone resections. For instance, those of skill in the art will appreciate that similar systems and algorithms may be used to optimize the fit of a spinal implant into a defined or desired joint space or gap between two vertebrae.

As another non-limiting example, those of skill in the art will recognize that resection based systems and methods are not limited to just planar resections, but that embodiments of the present invention may facilitate optimizing the fit of an implant onto a curved or other shaped resection.

In view of the foregoing, it will be seen that the several advantages of the invention are achieved and attained.

The embodiments were chosen and described in order to best explain the principles of the invention and its practical application to thereby enable others skilled in the art to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting. For example, while the figures illustrate the present invention as applied to knee arthroplasty, the present invention is equally applicable to other areas. Thus, the breadth and scope of the present invention should not be limited by any of the above-described exemplary embodiments, but should be defined only in accordance with the following claims appended hereto and their equivalents.

What is claimed is:

1. A method for pre-operatively optimizing a fit of an orthopaedic implant relative to an anatomy of an individual, the method comprising:
    receiving a three-dimensional anatomic model of the anatomy of the individual;
    receiving one or more simulated resection portions of the three-dimensional anatomic model;
    identifying, based on the three-dimensional anatomic model and the one or more simulated resection portions, one or more priority zones associated with the three-dimensional anatomic model;
    selecting, based on the three-dimensional anatomic model and the one or more simulated resection portions, an orthopaedic implant model corresponding to an orthopaedic implant and having an associated size;
    generating, based on the one or more priority zones, a first point set comprising a plurality of points at a periphery of the simulated resection portion;
    generating a second point set comprising a plurality of points at a periphery of the selected orthopaedic implant model;
    determining whether the position of the periphery of the selected orthopaedic implant model relative to the periphery of the simulated resection portion is optimal based on the first point set and the second point set; and
    verifying one or more of the position and the size of the orthopaedic implant.

2. The method of claim 1, wherein receiving a three-dimensional anatomic model comprises generating the three-dimensional anatomic model by segmenting imaging data of the patient's anatomy, wherein the imaging data comprises at least one of an MRI, CT, x-ray, or ultrasound.

3. The method of claim 1, wherein receiving one or more simulated resection portions comprises determining the one or more simulated resection portions based on one or more manual inputs from a user.

4. The method of claim 1, wherein receiving one or more simulated resection portions comprises automatically determining the one or more simulated resection portions based on the three-dimensional anatomic model to optimize biomechanical performance.

5. The method of claim 1, further comprising identifying an abnormal morphology of the three-dimensional anatomic model.

6. The method of claim 5, wherein identifying the abnormal morphology comprises identifying the abnormal morphology by applying a trained neural network to the one or more simulated resection portions.

7. The method of claim 5, wherein identifying the abnormal morphology comprises identifying the abnormal morphology by applying an automatic segmentation process to the one or more simulated resection portions.

8. The method of claim 1, wherein determining whether the position of the periphery of the selected orthopaedic implant model relative to the periphery of the simulated resection portion is optimal further comprises:
    determining whether a current position causes the periphery of the selected orthopaedic implant model to overhang the periphery of the simulated resection portion; and
    responsive to determining that the current position results in overhang, selecting a different orthopaedic implant model corresponding to an orthopaedic implant and having an associated size that is smaller than the selected orthopedic implant model.

9. The method of claim 1, wherein determining whether the position of the periphery of the selected orthopaedic implant model relative to the periphery of the simulated resection portion is optimal further comprises:
    determining whether a current position causes the periphery of the selected orthopaedic implant model to overhang the periphery of the simulated resection portion; and
    responsive to determining that the current position results in overhang, selecting a different orthopaedic implant model corresponding to an orthopaedic implant and having an associated size that is larger than the selected orthopedic implant model.

10. The method of claim 1, wherein the one or more priority zones are located in the anterior region.

11. The method of claim 1, wherein the one or more priority zones are located in the posterior region.

12. The method of claim 1, wherein the one or more priority zones are located in the medical region.

13. The method of claim 1, wherein the second point set is based on a grid system or a radial distribution associated with the three-dimensional anatomic model.

14. A system for pre-operatively optimizing a fit of an orthopaedic implant relative to an anatomy of an individual, the system comprising:
    a processing device; and
    a non-transitory, processor-readable storage medium in communication with the processing device, wherein the non-transitory, processor-readable storage medium contains one or more programming instructions that, when executed, cause the processing device to:
    receive a three-dimensional anatomic model of the anatomy of the individual;
    receive one or more simulated resection portions of the three-dimensional anatomic model;
    identify, based on the three-dimensional anatomic model and the one or more simulated resection portions, one or more priority zones associated with the three-dimensional anatomic model;
    select, based on the three-dimensional anatomic model and the one or more simulated resection portions, an orthopaedic implant model corresponding to an orthopaedic implant and having an associated size;
    generate, based on the one or more priority zones, a first point set comprising a plurality of points at a periphery of the simulated resection portion;
    generate a second point set comprising a plurality of points at a periphery of the selected orthopaedic implant model;
    determine whether the position of the periphery of the selected orthopaedic implant model relative to the periphery of the simulated resection portion is optimal based on the first point set and the second point set; and verify one or more of the position and the size of the orthopaedic implant.

15. The system of claim 14, wherein the one or more programming instructions that, when executed, cause the processing device to receive a three-dimensional anatomic model further comprises one or more programming instructions that, when executed, cause the processing device to generate the three-dimensional anatomic model by segmenting imaging data of the patient's anatomy, wherein the imaging data comprises at least one of an MRI, CT, x-ray, or ultrasound.

16. The system of claim 14, wherein the one or more programming instructions that, when executed, cause the processing device to receive one or more simulated resection portions further comprises one or more programming instructions that, when executed, cause the processing device to determine the one or more simulated resection portions based on one or more manual inputs from a user.

17. The system of claim 14, wherein the one or more programming instructions that, when executed, cause the processing device to receive one or more simulated resection portions further comprises one or more programming instructions that, when executed, cause the processing device to automatically determine the one or more simulated resection portions based on the three-dimensional anatomic model to optimize biomechanical performance.

18. The system of claim 14, further comprising one or more programming instructions that, when executed, cause the processing device to identify an abnormal morphology of the three-dimensional anatomic model.

19. The system of claim 18, wherein the one or more programming instructions that, when executed, cause the processing device to identify the abnormal morphology further comprises one or more programming instructions that, when executed, cause the processing device to identify the abnormal morphology by applying a trained neural network to the one or more simulated resection portions.

20. The system of claim 18, wherein the one or more programming instructions that, when executed, cause the processing device to identify the abnormal morphology further comprises one or more programming instructions that, when executed, cause the processing device to identify the abnormal morphology by applying an automatic segmentation process to the one or more simulated resection portions.

21. The system of claim 14, wherein the one or more programming instructions that, when executed, cause the processing device to determine whether the position of the periphery of the selected orthopaedic implant model relative to the periphery of the simulated resection portion is optimal further comprises one or more programming instructions that, when executed, cause the processing device to:

determine whether a current position causes the periphery of the selected orthopaedic implant model to overhang the periphery of the simulated resection portion; and responsive to determining that the current position results in overhang, select a different orthopaedic implant model corresponding to an orthopaedic implant and having an associated size that is smaller than the selected orthopedic implant model.

22. The system of claim 14, wherein the one or more programming instructions that, when executed, cause the processing device to determine whether the position of the periphery of the selected orthopaedic implant model relative to the periphery of the simulated resection portion is optimal further comprises one or more programming instructions that, when executed, cause the processing device to:

determine whether a current position causes the periphery of the selected orthopaedic implant model to overhang the periphery of the simulated resection portion; and responsive to determining that the current position results in overhang, select a different orthopaedic implant model corresponding to an orthopaedic implant and having an associated size that is larger than the selected orthopedic implant model.

* * * * *